United States Patent
Barachant et al.

(10) Patent No.: US 10,772,519 B2
(45) Date of Patent: Sep. 15, 2020

(54) METHODS AND APPARATUS FOR PROVIDING SUB-MUSCULAR CONTROL

(71) Applicant: Facebook Technologies, LLC, Menlo Park, CA (US)

(72) Inventors: Alexandre Barachant, Brooklyn, NY (US); Patrick Kaifosh, New York, NY (US); Daniel Wetmore, Brooklyn, NY (US)

(73) Assignee: Facebook Technologies, LLC, Menlo Park, CA (US)

( * ) Notice: Subject to any disclaimer, the term of this patent is extended or adjusted under 35 U.S.C. 154(b) by 7 days.

(21) Appl. No.: 16/389,419

(22) Filed: Apr. 19, 2019

(65) Prior Publication Data

US 2019/0357787 A1 Nov. 28, 2019

Related U.S. Application Data

(60) Provisional application No. 62/676,567, filed on May 25, 2018.

(51) Int. Cl.
| | |
|---|---|
| *G09B 19/00* | (2006.01) |
| *A61B 5/04* | (2006.01) |
| *A61B 5/0488* | (2006.01) |
| *A61B 5/00* | (2006.01) |

(Continued)

(52) U.S. Cl.
CPC ...... *A61B 5/04001* (2013.01); *A61B 5/04004* (2013.01); *A61B 5/0488* (2013.01); *A61B 5/6824* (2013.01); *A61B 5/6831* (2013.01); *G06F 3/015* (2013.01); *G06F 3/016* (2013.01);

(Continued)

(58) Field of Classification Search
None
See application file for complete search history.

(56) References Cited

U.S. PATENT DOCUMENTS

| | | |
|---|---|---|
| 4,055,168 A | 10/1977 | Miller et al. |
| 4,896,120 A | 1/1990 | Kamil |
| 5,625,577 A | 4/1997 | Kunii et al. |

(Continued)

FOREIGN PATENT DOCUMENTS

| | | |
|---|---|---|
| CA | 2902045 A1 | 8/2014 |
| CA | 2921954 A1 | 2/2015 |

(Continued)

OTHER PUBLICATIONS

International Preliminary Report on Patentability for International Application No. PCT/US2017/043686 dated Feb. 7, 2019.

(Continued)

*Primary Examiner* — James B Hull
(74) *Attorney, Agent, or Firm* — FisherBroyles, LLP

(57) ABSTRACT

Methods and apparatus for generating a control signal based on sub-muscular activation. Information for a first sub-muscular control channel of a plurality of sub-muscular control channels is derived from the plurality of neuromuscular signals. Each of the plurality of sub-muscular control channels is configured to process information associated with activation of one or more sub-muscular structures. A control signal is generated based on the derived information for the first sub-muscular control channel and the control signal is provided to a control interface to control an operation of a device.

20 Claims, 10 Drawing Sheets

(51) Int. Cl.
*G06F 3/01* (2006.01)
*G06N 5/04* (2006.01)

(52) U.S. Cl.
CPC .............. *G06F 3/017* (2013.01); *G06N 5/04* (2013.01); *G09B 19/00* (2013.01)

(56) References Cited

U.S. PATENT DOCUMENTS

| | | | |
|---|---|---|---|
| 6,005,548 | A | 12/1999 | Latypov et al. |
| 6,009,210 | A | 12/1999 | Kand |
| 6,244,873 | B1 | 6/2001 | Hill et al. |
| 6,411,843 | B1 | 6/2002 | Zarychta |
| 6,658,287 | B1 | 12/2003 | Litt et al. |
| 6,720,984 | B1 | 4/2004 | Jorgensen et al. |
| 6,774,885 | B1 | 8/2004 | Even-Zohar |
| 6,942,621 | B2 | 9/2005 | Avinash et al. |
| 7,089,148 | B1 | 8/2006 | Bachmann et al. |
| 7,351,975 | B2 | 4/2008 | Brady et al. |
| 7,574,253 | B2 | 8/2009 | Edney et al. |
| 7,580,742 | B2 | 8/2009 | Tan et al. |
| 7,787,946 | B2 | 8/2010 | Stahmann et al. |
| 7,805,386 | B2 | 9/2010 | Greer |
| 7,901,368 | B2 | 3/2011 | Flaherty et al. |
| 8,170,656 | B2 | 5/2012 | Tan et al. |
| 8,190,249 | B1 | 5/2012 | Gharieb et al. |
| 8,311,623 | B2 | 11/2012 | Sanger |
| 8,351,651 | B2 | 1/2013 | Lee |
| 8,421,634 | B2 | 4/2013 | Tan et al. |
| 8,435,191 | B2 | 5/2013 | Barboutis et al. |
| 8,437,844 | B2 | 5/2013 | Syed Momen et al. |
| 8,447,704 | B2 | 5/2013 | Tan et al. |
| 8,484,022 | B1 | 7/2013 | Vanhoucke |
| 8,718,980 | B2 | 5/2014 | Garudadri et al. |
| 8,744,543 | B2 | 6/2014 | Li et al. |
| 8,754,862 | B2 | 6/2014 | Zaliva |
| D717,685 | S | 11/2014 | Bailey et al. |
| 8,880,163 | B2 | 11/2014 | Barachant et al. |
| 8,890,875 | B2 | 11/2014 | Jammes et al. |
| 8,892,479 | B2 | 11/2014 | Tan et al. |
| 9,037,530 | B2 | 5/2015 | Tan et al. |
| D742,272 | S | 11/2015 | Bailey et al. |
| 9,218,574 | B2 | 12/2015 | Phillipps et al. |
| 9,235,934 | B2 | 1/2016 | Mandella et al. |
| 9,240,069 | B1 | 1/2016 | Li |
| 9,278,453 | B2 | 3/2016 | Assad |
| 9,299,248 | B2 | 3/2016 | Lake et al. |
| D756,359 | S | 5/2016 | Bailey et al. |
| 9,367,139 | B2 | 6/2016 | Ataee et al. |
| 9,372,535 | B2 | 6/2016 | Bailey et al. |
| 9,389,694 | B2 | 7/2016 | Ataee et al. |
| 9,408,316 | B2 | 8/2016 | Bailey et al. |
| 9,459,697 | B2 | 10/2016 | Bedikian et al. |
| 9,483,123 | B2 | 11/2016 | Aleem et al. |
| 9,597,015 | B2 | 3/2017 | McNames et al. |
| 9,600,030 | B2 | 3/2017 | Bailey et al. |
| 9,612,661 | B2 | 4/2017 | Wagner et al. |
| 9,613,262 | B2 | 4/2017 | Holz |
| 9,659,403 | B1 | 5/2017 | Horowitz |
| 9,687,168 | B2 | 6/2017 | John |
| 9,696,795 | B2 | 7/2017 | Marcolina et al. |
| 9,720,515 | B2 | 8/2017 | Wagner et al. |
| 9,741,169 | B1 | 8/2017 | Holz |
| 9,766,709 | B2 | 9/2017 | Holz |
| 9,785,247 | B1 | 10/2017 | Horowitz et al. |
| 9,788,789 | B2 | 10/2017 | Bailey |
| 9,864,431 | B2 | 1/2018 | Keskin et al. |
| 9,867,548 | B2 | 1/2018 | Le et al. |
| 9,880,632 | B2 | 1/2018 | Ataee et al. |
| 9,891,718 | B2 | 2/2018 | Connor |
| 10,042,422 | B2 | 8/2018 | Morun et al. |
| 10,070,799 | B2 | 9/2018 | Ang et al. |
| 10,078,435 | B2 | 9/2018 | Noel |
| 10,101,809 | B2 | 10/2018 | Morun et al. |
| 10,152,082 | B2 | 12/2018 | Bailey |
| 10,188,309 | B2 | 1/2019 | Morun et al. |
| 10,199,008 | B2 | 2/2019 | Aleem et al. |
| 10,203,751 | B2 | 2/2019 | Keskin et al. |
| 10,216,274 | B2 | 2/2019 | Chapeskie et al. |
| 10,251,577 | B2 | 4/2019 | Morun et al. |
| 10,310,601 | B2 | 6/2019 | Morun et al. |
| 10,331,210 | B2 | 6/2019 | Morun et al. |
| 10,362,958 | B2 | 7/2019 | Morun et al. |
| 10,409,371 | B2 | 9/2019 | Kaifosh et al. |
| 2003/0144829 | A1 | 7/2003 | Geatz et al. |
| 2003/0171921 | A1 | 9/2003 | Manabe et al. |
| 2003/0184544 | A1 | 10/2003 | Prudent |
| 2004/0092839 | A1 | 5/2004 | Shin et al. |
| 2007/0172797 | A1 | 7/2007 | Hada et al. |
| 2007/0177770 | A1 | 8/2007 | Derchak et al. |
| 2007/0256494 | A1 | 11/2007 | Nakamura et al. |
| 2007/0285399 | A1 | 12/2007 | Lund |
| 2008/0052643 | A1 | 2/2008 | Ike et al. |
| 2008/0214360 | A1 | 9/2008 | Stirling et al. |
| 2008/0221487 | A1 | 9/2008 | Zohar et al. |
| 2009/0082692 | A1 | 3/2009 | Hale et al. |
| 2009/0082701 | A1 | 3/2009 | Zohar et al. |
| 2009/0112080 | A1 | 4/2009 | Matthews |
| 2009/0124881 | A1 | 5/2009 | Rytky |
| 2009/0326406 | A1 | 12/2009 | Tan et al. |
| 2009/0327171 | A1 | 12/2009 | Tan et al. |
| 2010/0030532 | A1 | 2/2010 | Arora et al. |
| 2010/0063794 | A1 | 3/2010 | Hernandez-Rebollar |
| 2010/0106044 | A1 | 4/2010 | Linderman |
| 2010/0280628 | A1 | 11/2010 | Sankai |
| 2010/0292617 | A1 | 11/2010 | Lei et al. |
| 2010/0293115 | A1 | 11/2010 | Seyed Momen |
| 2010/0315266 | A1 | 12/2010 | Gunawardana et al. |
| 2011/0077484 | A1 | 3/2011 | Van Slyke et al. |
| 2011/0092826 | A1 | 4/2011 | Lee et al. |
| 2012/0066163 | A1 | 3/2012 | Balls et al. |
| 2012/0188158 | A1 | 7/2012 | Tan et al. |
| 2012/0265480 | A1 | 10/2012 | Oshima |
| 2012/0283526 | A1 | 11/2012 | Gommesen et al. |
| 2013/0077820 | A1 | 3/2013 | Marais et al. |
| 2013/0141375 | A1 | 6/2013 | Ludwig et al. |
| 2013/0207889 | A1 | 8/2013 | Chang et al. |
| 2013/0217998 | A1 | 8/2013 | Mahfouz et al. |
| 2013/0232095 | A1 | 9/2013 | Tan et al. |
| 2013/0317382 | A1 | 11/2013 | Le |
| 2013/0317648 | A1 | 11/2013 | Assad |
| 2014/0052150 | A1 | 2/2014 | Taylor et al. |
| 2014/0092009 | A1 | 4/2014 | Yen et al. |
| 2014/0098018 | A1 | 4/2014 | Kim et al. |
| 2014/0196131 | A1 | 7/2014 | Lee |
| 2014/0198034 | A1 | 7/2014 | Bailey et al. |
| 2014/0198035 | A1 | 7/2014 | Bailey et al. |
| 2014/0223462 | A1 | 8/2014 | Aimone et al. |
| 2014/0240103 | A1 | 8/2014 | Lake et al. |
| 2014/0240223 | A1 | 8/2014 | Lake et al. |
| 2014/0245200 | A1 | 8/2014 | Holz |
| 2014/0249397 | A1 | 9/2014 | Lake et al. |
| 2014/0278441 | A1 | 9/2014 | Ton et al. |
| 2014/0297528 | A1 | 10/2014 | Agrawal et al. |
| 2014/0304665 | A1 | 10/2014 | Holz |
| 2014/0334083 | A1 | 11/2014 | Bailey |
| 2014/0344731 | A1 | 11/2014 | Holz |
| 2014/0355825 | A1 | 12/2014 | Kim et al. |
| 2014/0365163 | A1 | 12/2014 | Jallon |
| 2014/0376773 | A1 | 12/2014 | Holz |
| 2015/0006120 | A1 | 1/2015 | Sett et al. |
| 2015/0010203 | A1 | 1/2015 | Muninder et al. |
| 2015/0025355 | A1 | 1/2015 | Bailey et al. |
| 2015/0029092 | A1 | 1/2015 | Holz et al. |
| 2015/0035827 | A1 | 2/2015 | Yamaoka et al. |
| 2015/0045699 | A1 | 2/2015 | Mokaya et al. |
| 2015/0051470 | A1 | 2/2015 | Bailey et al. |
| 2015/0057770 | A1 | 2/2015 | Bailey et al. |
| 2015/0070270 | A1 | 3/2015 | Bailey et al. |
| 2015/0070274 | A1 | 3/2015 | Morozov |
| 2015/0084860 | A1 | 3/2015 | Aleem et al. |
| 2015/0109202 | A1 | 4/2015 | Ataee et al. |
| 2015/0124566 | A1 | 5/2015 | Lake et al. |
| 2015/0128094 | A1 | 5/2015 | Baldwin et al. |
| 2015/0141784 | A1 | 5/2015 | Morun et al. |

(56) References Cited

U.S. PATENT DOCUMENTS

| | | |
|---|---|---|
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0346701 A1 | 12/2015 | Gordon et al. |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0144172 A1 | 5/2016 | Hsueh et al. |
| 2016/0162604 A1 | 6/2016 | Xioli et al. |
| 2016/0187992 A1 | 6/2016 | Yamamoto et al. |
| 2016/0235323 A1 | 8/2016 | Tadi et al. |
| 2016/0262687 A1* | 9/2016 | Vaidyanathan ...... A61B 5/1123 |
| 2016/0274758 A1 | 9/2016 | Bailey |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0188980 A1 | 7/2017 | Ash |
| 2017/0259167 A1 | 9/2017 | Cook et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0088765 A1 | 3/2018 | Bailey |
| 2018/0095630 A1 | 4/2018 | Bailey |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0025919 A1 | 1/2019 | Tadi et al. |
| 2019/0033967 A1 | 1/2019 | Morun et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |

FOREIGN PATENT DOCUMENTS

| | | |
|---|---|---|
| CA | 2939644 A1 | 8/2015 |
| CN | 1838933 A | 9/2006 |
| CN | 105190578 A | 12/2015 |
| CN | 106102504 A | 11/2016 |
| EP | 2198521 B1 | 6/2012 |
| EP | 2959394 A1 | 12/2015 |
| EP | 3104737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | WO 2008/109248 A2 | 9/2008 |
| WO | WO 2009/042313 A1 | 4/2009 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |

OTHER PUBLICATIONS

International Preliminary Report on Patentability for International Application No. PCT/US2017/043693 dated Feb. 7, 2019.
International Preliminary Report on Patentability for International Application No. PCT/US2017/043791 dated Feb. 7, 2019.
International Preliminary Report on Patentability for International Application No. PCT/US2017/043792 dated Feb. 7, 2019.
International Search Report and Written Opinion for International Application No. PCT/US2017/043686 dated Oct. 6, 2017.
International Search Report and Written Opinion for International Application No. PCT/US2017/043693 dated Oct. 6, 2017.
International Search Report and Written Opinion for International Application No. PCT/US2017/043791 dated Oct. 5, 2017.
International Search Report and Written Opinion for International Application No. PCT/US2017/043792 dated Oct. 5, 2017.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.

(56) References Cited

OTHER PUBLICATIONS

International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US2019/028299 dated Aug. 9, 2019.
Invitation to Pay Additional Fees for International Application No. PCT/US2019/031114 dated Aug. 6, 2019.
International Search Report and Written Opinion for International Application No. PCT/US19/20065 dated May 16, 2019.
Arkenbout et al., Robust Hand Motion Tracking through Data Fusion of 5DT Data Glove and Nimble VR Kinect Camera Measurements. Sensors. 2015;15:31644-71.
Benko et al., Enhancing Input on and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Davoodi et al., Development of a Physics-Based Target Shooting Game to Train Amputee Users of Multijoint Upper Limb Prostheses. Presence. Massachusetts Institute of Technology. 2012;21(1):85-95.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.
Gallina et al., Surface EMG Biofeedback. Surface Electromyography: Physiology, Engineering, and Applications. 2016:485-500.
Gopura et al., A Human Forearm and wrist motion assist exoskeleton robot with EMG-based fuzzy-neuro control. Proceedings of the 2nd IEEE/RAS-EMBS International Conference on Biomedical Robotics and Biomechatronics. Oct. 19-22, 2008. 6 pages.
Hauschild et al., A Virtual Reality Environment for Designing and Fitting Neural Prosthetic Limbs. IEEE Transactions on Neural Systems and Rehabilitation Engineering. 2007;15(1):9-15.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.
Kim et al., Real-Time Human Pose Estimation and Gesture Recognition from Depth Images Using Superpixels and SVM Classifier. Sensors. 2015;15:12410-27.
Koerner, Design and Characterization of the Exo-Skin Haptic Device: A Novel Tendon Actuated Textile Hand Exoskeleton. 2017. 5 pages.
Lee et al., Motion and Force Estimation System of Human Fingers. Journal of Institute of Control, Robotics and Systems. 2011;17(10):1014-1020.
Li et al., Motor Function Evaluation of Hemiplegic Upper-Extremities Using Data Fusion from Wearable Inertial and Surface EMG Sensors. Sensors. MDPI. 2017;17(582):1-17.
Lopes et al., Hand/arm gesture segmentation by motion using IMU and EMG sensing. ScienceDirect. Elsevier. Procedia Manufacturing. 2017;11:107-13.
Martin et al., A Novel Approach of Prosthetic Arm Control using Computer Vision, Biosignals, and Motion Capture. IEEE. 2014. 5 pages.
McIntee, A Task Model of Free-Space Movement-Based Gestures. Dissertation. Graduate Faculty of North Carolina State University. Computer Science. 2016. 129 pages.
Mendes et al., Sensor Fusion and Smart Sensor in Sports and Biomedical Applications. Sensors. 2016;16(1569):1-31.
Naik et al., Source Separation and Identification issues in bio signals: A solution using Blind source separation. Intech. 2009. 23 pages.
Naik et al., Subtle Hand gesture identification for HCI using Temporal Decorrelation Source Separation BSS of surface EMG. Digital Image Computing Techniques and Applications. IEEE Computer Society. 2007;30-7.
Negro et al., Multi-channel intramuscular and surface EMG decomposition by convolutive blind source separation. Journal of Neural Engineering. 2016;13:1-17.
Saponas et al., Demonstrating the Feasibility of Using Forearm Electromyography for Muscle-Computer Interfaces. CHI 2008 Proceedings. Physiological Sensing for Input. 2008:515-24.
Saponas et al., Enabling Always-Available Input with Muscle-Computer Interfaces. UIST '09. 2009:167-76.
Saponas et al., Making Muscle-Computer Interfaces More Practical. CHI 2010: Brauns and Brawn. 2010:851-4.
Sartori et al., Neural Data-Driven Musculoskeletal Modeling for Personalized Neurorehabilitation Technologies. IEEE Transactions on Biomedical Engineering. 2016;63(5):879-93.
Sauras-Perez et al., A Voice and Pointing Gesture Interaction System for Supporting Human Spontaneous Decisions in Autonomous Cars. Clemson University. All Dissertations. 2017. 174 pages.
Shen et al., I am a Smartwatch and I can Track my User's Arm. University of Illinois at Urbana-Champaign. MobiSys' 16. 12 pages.
Son et al., Evaluating the utility of two gestural discomfort evaluation methods. PLOS One. 2017. 21 pages.
Strbac et al., Microsoft Kinect-Based Artificial Perception System for Control of Functional Electrical Stimulation Assisted Grasping. Hindawi Publishing Corporation. BioMed Research International. 2014. 13 pages.
Torres, Myo Gesture Control Armband. PCMag. Https://www.pcmag.com/article2/0,2817,2485462,00.asp 2015. 9 pages.
Valero-Cuevas et al., Computational Models for Neuromuscular Function. NIH Public Access Author Manuscript. Jun. 16, 2011. 52 pages.
Wodzinski et al., Sequential Classification of Palm Gestures Based on A* Algorithm and MLP Neural Network for Quadrocopter Control. Metrol. Meas. Syst., 2017;24(2):265-76.
Xue et al., Multiple Sensors Based Hand Motion Recognition Using Adaptive Directed Acyclic Graph. Applied Sciences. MDPI. 2017;7(358):1-14.
Yang et al., Surface EMG based handgrip force predictions using gene expression programming. Neurocomputing. 2016;207:568-579.

\* cited by examiner

US 10,772,519 B2

METHODS AND APPARATUS FOR PROVIDING SUB-MUSCULAR CONTROL

RELATED APPLICATIONS

This Application claims priority under 35 USC § 119(e) to U.S. Provisional Application Ser. No. 62/676,567, filed May 25, 2018, entitled "METHODS AND APPARATUS FOR PROVIDING SUB-MUSCULAR CONTROL", which is incorporated by reference in its entirety.

BACKGROUND

Neuromuscular signals arising from the human central nervous system may reflect neural activation that results in the contraction of one or more muscles in the human body. Neuromuscular sensors, an example of which includes electromyography (EMG) sensors, placed on the surface of the human body record neuromuscular activity produced when skeletal muscle cells are activated. The neuromuscular activity measured by neuromuscular sensors may result from neural activation, muscle excitation, muscle contraction, or a combination of the neural activation and muscle contraction. Electrical signals recorded by neuromuscular sensors can be used to assess neuromuscular dysfunction in patients with motor control disorders and in some applications as control signals for devices such as prosthetic limbs.

SUMMARY

Coordinated movements of skeletal muscles in the human body that collectively result in the performance of a motor task originate with neural signals arising in the central nervous system. The neural signals travel from the central nervous system to muscles via spinal motor neurons, each of which has a cell body in the spinal cord and axon terminals on one or more muscle fibers. In response to receiving the neural signals, the muscle fibers contract, resulting in muscle movement. A spinal motor neuron and the muscle fiber(s) it innervates are collectively referred to as a "motor unit." Muscles typically include muscle fibers from hundreds of motor units and simultaneous contraction of muscle fibers in multiple motor units is usually required for muscle contraction that results in muscle movement.

Neuromuscular sensors such as EMG sensors record biological signals that result in motor activity, such as contraction of a muscle. In the case of EMG sensors arranged on the surface of the human body, the biological signals recorded relate to the generation of action potentials in muscle fibers. Some embodiments are directed to analyzing neuromuscular signals to identify patterns of activation associated with sub-muscular biological structures (e.g., individual motor units or groups of motor units). Control signals determined based on activation of sub-muscular structures may be used to control the operation of devices.

Some embodiments are directed to a computerized system. The computerized system comprises a plurality of neuromuscular sensors configured to record a plurality of neuromuscular signals from a user, wherein the plurality of neuromuscular sensors are arranged on one or more wearable devices and at least one computer processor. The at least one computer processor is programmed to derive, from the plurality of neuromuscular signals, information for a first sub-muscular control channel of a plurality of sub-muscular control channels, wherein each of the plurality of sub-muscular control channels is configured to process information associated with activation of one or more sub-muscular structures, generate, based on the derived information for the first sub-muscular control channel, a control signal, and provide the control signal to a control interface to control an operation of a device.

In at least one aspect, the at least one computer processor is further programmed to provide, as input to a trained inference model, the derived information for the first sub-muscular control channel, and wherein generating the control signal comprises generating the control signal based on the output of the trained inference model.

In at least one aspect, the at least one computer processor is further programmed to provide as input to a trained inference model, the plurality of neuromuscular signals, and wherein deriving information for the first sub-muscular control channel comprises deriving the information based on processing of the plurality of neuromuscular signals by the trained inference model.

In at least one aspect, deriving information for the first sub-muscular control channel comprises decomposing the plurality of neuromuscular signals into signal components characterizing the plurality of sub-muscular control channels.

In at least one aspect, the first sub-muscular control channel is configured to process information arising from activation of a single motor unit.

In at least one aspect, a second sub-muscular control channel of the plurality of sub-muscular control channels is configured to process information arising from activation of a plurality of motor units.

In at least one aspect, the first sub-muscular control channel is configured to process information arising from activation of a combination of at least one first sub-muscular structure associated with a first muscle and at least one second sub-muscular structure associated with a second muscle.

In at least one aspect, the computerized system further comprises at least one auxiliary sensor configured to record an auxiliary signal simultaneously with the recording of the plurality of neuromuscular signals from the user, wherein the at least one auxiliary sensor is arranged on the one or more wearable devices.

In at least one aspect, the at least one auxiliary sensor comprises at least one inertial measurement unit.

In at least one aspect, the at least one computer processor is further programmed to store a representation of the derived information for the first sub-muscular control channel determined during a first session, and calibrate neuromuscular signal data recorded from the user during a second session after the first session, wherein the calibration is performed based, at least in part, on the stored representation of the derived information for the first sub-muscular control channel determined during the first session.

Some embodiments are directed to a computerized system for training a user to activate sub-muscular structures. The system comprises a plurality of neuromuscular sensors configured to record a plurality of neuromuscular signals from the user as the user activates one or more sub-muscular structures, wherein the plurality of neuromuscular sensors are arranged on one or more wearable devices and at least one computer processor. The at least one computer processor is programmed to provide feedback to the user based on the plurality of neuromuscular signals, wherein the feedback includes information about a pattern of activation identified in the plurality of neuromuscular signals, adjust the feedback provided to the user based on the recorded plurality of neuromuscular signals, and store information mapping the pattern of activation identified in the plurality of neuromuscular signals to a control signal.

In at least one aspect, the sub-muscular structure is an individual motor unit.

In at least one aspect, providing feedback to the user based on the plurality of neuromuscular signals comprises generating the feedback from an unprocessed version of the plurality of neuromuscular signals.

In at least one aspect, the at least one computer processor is further programmed to determine, based on the plurality of neuromuscular signals, from among a plurality of sub-muscular structures, which one of the plurality of sub-muscular structures the user has activated, and wherein providing feedback to the user based on the plurality of neuromuscular signals comprises providing first feedback when it is determined that a first sub-muscular structure of the plurality of sub-muscular structures has been activated and providing second feedback when it is determined that a second sub-muscular structure of the plurality of sub-muscular structures has been activated.

In at least one aspect, the first feedback and the second feedback have different characteristics to enable the user to distinguish between the first and second feedback.

In at least one aspect, the first feedback comprises auditory feedback having a first pitch, and wherein the second feedback comprises auditory feedback having a second pitch different from the first pitch.

In at least one aspect, the feedback comprises feedback selected from the group consisting of auditory feedback, visual feedback, tactile feedback, and feedback provided via electrical stimulation.

In at least one aspect, the at least one computer processor is further programmed to derive a control signal based on the plurality of neuromuscular signals, and provide the control signal to a device having an operation that the user is trying to control, wherein providing feedback to the user based on the plurality of neuromuscular signals comprises changing a behavior of the device based on the control signal.

In at least one aspect, the device comprises a display.

In at least one aspect, deriving the control signal comprises providing as input to an inference model, the plurality of neuromuscular signals or information derived from the plurality of neuromuscular signals, and deriving the control signal based on an output of the inference model.

In at least one aspect, the at least one computer processor is further programmed to train an inference model to map the pattern of activation determined from the plurality of neuromuscular signals to one or more sub-muscular activation patterns and wherein storing the information mapping the pattern of activation identified in the plurality of neuromuscular signals to a control signal comprises storing the trained inference model.

In at least one aspect, the at least one computer processor is further programmed to computationally map the one or more sub-muscular activation patterns the control signal.

In at least one aspect, storing the information mapping the pattern of activation identified in the plurality of neuromuscular signals to a control signal comprises storing information describing the pattern of activation determined from the plurality of neuromuscular signals.

In at least one aspect, the at least one computer processor is further programmed to identify, based on the plurality of neuromuscular signals, a plurality of sub-muscular structures activated by the user.

In at least one aspect, identifying the plurality of sub-muscular structures activated by the user comprises decomposing the plurality of neuromuscular signals into signal components that characterize activation of a particular sub-muscular structure, and mapping information derived from the plurality of neuromuscular signals to the one or more control signals comprises mapping the signal components that characterize activation of the particular sub-muscular structure to the one or more control signals.

In at least one aspect, the at least one computer processor is further programmed to identify, based on the plurality of neuromuscular signals, a plurality of sub-muscular structures activated by the user, select, based on characteristics of activation associated with each of the plurality of sub-muscular structures activated by the user, a subset of sub-muscular structures to use for training, and wherein the feedback includes information about a pattern of activation for the subset of sub-muscular structures.

In at least one aspect, the characteristics of activation associated with the sub-muscular structure are selected from the group consisting of a type of motor unit associated with the sub-muscular structure, a motor unit action potential amplitude associated with the sub-muscular structure, a similarity of a waveform for activation of the sub-muscular structure to waveforms for activation of other sub-muscular structures, and activation rate and timing statistics associated with activation of the sub-muscular structure.

In at least one aspect, the computerized system further comprises at least one storage device configured to store spatiotemporal information about at least one activated sub-muscular structure.

In at least one aspect, the computerized system further comprises a user interface configured to instruct a user to activate a particular sub-muscular structure, wherein the plurality of neuromuscular sensors is configured to record the plurality of neuromuscular signals in response to the user attempting to activate the particular sub-muscular structure indicated by the user interface.

In at least one aspect, instructing the user to activate the particular sub-muscular structure comprises instructing the user to activate a plurality of sub-muscular structures in sequence, and wherein the at least one computer processor is further programmed to perform a calibration based, at least in part, on the plurality of neuromuscular signals.

Some embodiments are directed to a computer-implemented method of controlling a device. The method comprises receiving a plurality of neuromuscular signals recorded from a plurality of neuromuscular sensors arranged on one or more wearable devices worn by a user, deriving, from the plurality of neuromuscular signals, information for a first sub-muscular control channel of a plurality of sub-muscular control channels, wherein each of the plurality of sub-muscular control channels is configured to process information associated with activation of one or more sub-muscular structures, generating a control signal based on the derived information for the first sub-muscular control channel, and providing the control signal to a control interface to control an operation of a device.

Some embodiments are directed to a computer-implemented method of training a user to activate sub-muscular structures. The method comprises recording a plurality of neuromuscular signals from a plurality of neuromuscular sensors arranged on one or more wearable devices worn by a user, providing feedback to the user based on the plurality of neuromuscular signals, wherein the feedback includes information about a pattern of activation identified in the plurality of neuromuscular signals, adjusting the feedback provided to the user based on the recorded plurality of neuromuscular signals, and storing information mapping the pattern of activation identified in the plurality of neuromuscular signals to a control signal.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIG. 10A illustrates a wearable portion of the computer-based system and FIG. 10B illustrates a dongle portion connected to a computer, wherein the dongle portion is configured to communicate with the wearable portion.

DETAILED DESCRIPTION

Figure 1:
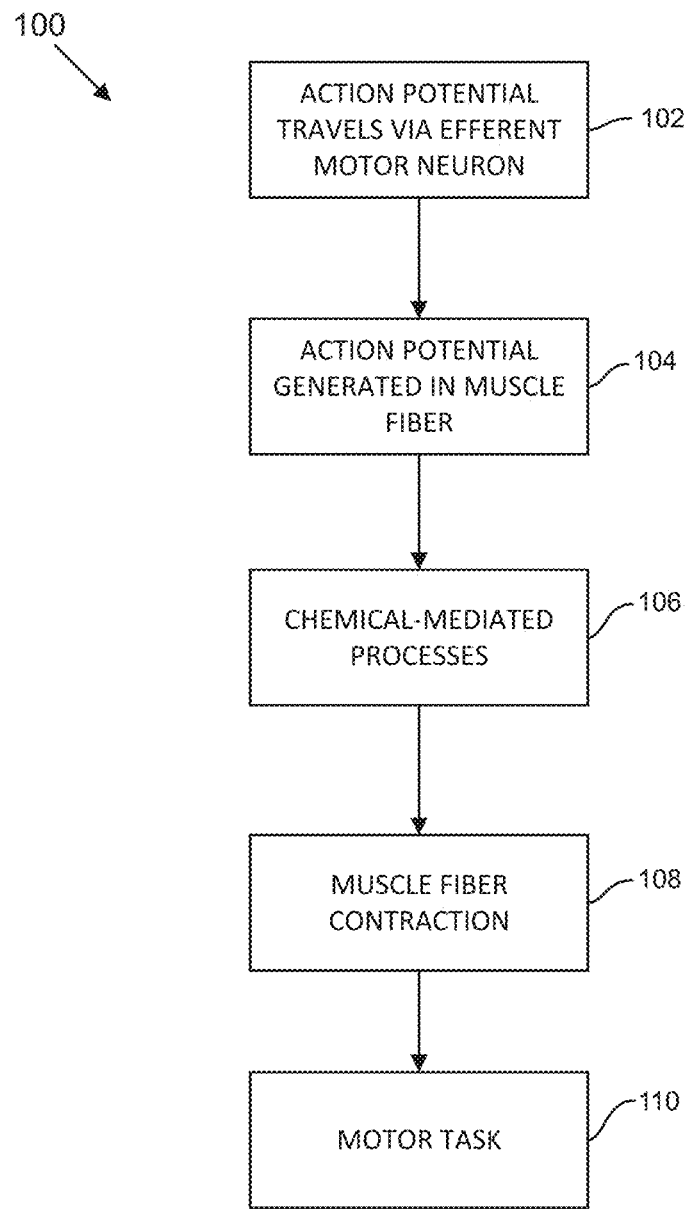
FIG. 1 is a flowchart of a biological process for performing a motor task in accordance with some embodiments of the technology described herein.

FIG. 1 illustrates a flowchart of a biological process 100 for initiating a motor task by the coordinated movement of one or more muscles. In act 102, action potentials are generated in one or more efferent spinal motor neurons. The motor neurons carry the neuronal signal away from the central nervous system and toward skeletal muscles in the periphery. For each motor neuron in which an action potential is generated, the action potential travels along the axon of motor neuron from its body in the spinal cord where the action potential is generated to the axon terminals of the motor neuron that innervate muscle fibers included in skeletal muscles. A motor neuron and the muscle fibers that it innervates are referred to herein as a motor unit. Muscle fibers in a motor unit are activated together in response to an action potential generated in the corresponding motor neuron of the motor unit. Individual muscles typically include muscle fibers from hundreds of motor units with the simultaneous contraction of muscle fibers in many motor units resulting in muscle contraction evidenced as perceptible muscle movement.

A chemical synapse formed at the interface between an axon terminal of a spinal motor neuron and a muscle fiber is called a neuromuscular junction. As an action potential transmitted along the axon of a motor neuron reaches the neuromuscular junction, process 100 proceeds to act 104, where an action potential is generated in the muscle fiber as a result of chemical activity at the neuromuscular junction. In particular, acetylcholine released by the motor neuron diffuses across the neuromuscular junction and binds with receptors on the surface of the muscle fiber triggering a depolarization of the muscle fiber. Although neuromuscular signals sensed on the body surface generated by the depolarization of individual muscle fibers are small (e.g., less than 100 µV), the collective action of multiple muscle fibers conducting simultaneously results in a detectable voltage potential that may be recorded by neuromuscular sensors (e.g., EMG sensors) located on the surface of the body. As noted above, the collective conduction of muscle fibers from many motor units results in muscle contraction and perceptible motion. Accordingly, when a user performs a movement or gesture, the corresponding recorded neuromuscular signals include contributions from multiple activated motor units.

Following generation of an action potential in the muscle fiber, process 100 proceeds to act 106, where the propagation of the action potential in the muscle fiber results in a series of chemical-mediated processes within the muscle fiber. For example, depolarization of a muscle fiber results in an influx of calcium ions into the muscle fiber. Calcium ions inside the muscle fiber bind with troponin complexes causing the troponin complexes to separate from myosin binding sites on actin filaments in the muscle fiber, thereby exposing the myosin binding sites.

Following these chemical-mediated processes, process 100 proceeds to act 108, where the muscle fiber contracts. Muscle fiber contraction is achieved due to the binding of exposed myosin heads with actin filaments in the muscle fiber creating cross-bridge structures. Process 100 then proceeds to act 110, where the collective contraction of muscle fibers in one or more muscles results in the performance of a motor task.

As the tension of a muscle increases during performance of a motor task, the firing rates of active neurons increases and additional neurons may become active, which is a process referred to as motor unit recruitment. The pattern by which neurons become active and increase their firing rate is stereotyped, such that the expected motor unit recruitment patterns define an activity manifold associated with standard or normal movement. Some embodiments are directed to teaching a user to activate a single motor unit or a group of motor units that are "off-manifold," in that the pattern of motor unit activation is different than an expected or typical motor unit recruitment pattern. Such off-manifold activation is referred to herein as, "sub-muscular activation" or "activation of a sub-muscular structure," where a sub-muscular structure refers to the single motor unit or the group of motor units associated with the off-manifold activation. Examples of off-manifold motor unit recruitment patterns include, but are not limited to, selectively activating a high-threshold motor unit without activating a lower-threshold motor unit that would normally be activated earlier in the recruitment order and modulating the firing rate of a motor unit across a substantial range without modulating the activity of other neurons that would normally be co-modulated in typical motor recruitment patterns. Sub-muscular activation is used in accordance with some embodiments of the technology described herein to generate control information, as described in more detail below.

When a user performs a motor task, such as moving their arm, a group of muscles necessary to perform the motor task is activated. When the motor task is performed while the user is wearing a wearable device that includes neuromuscular sensors, the neuromuscular signals recorded by the sensors on the surface of the body correspond to superimposed activity of all motor units in the muscles in the group activated during performance of the motor task. The neuromuscular signals may be analyzed and mapped to control signals to control a device based on the type of movement or gesture that the user performs. For example, if the user performs a thumbs-up gesture with their hand, a corresponding control signal to select an object in a user interface may be generated. The mapping between sensor signals and control signals may be implemented, for example, using an inference model trained to associate particular sensor signal inputs with control signal outputs. In some implementations, the inference model(s) can include one or more statistical models, one or more machine learning models, and/or a combination of one or more statistical model(s) and/or one or more machine learning model(s). A further discussion of the implementation of the inference model is provided below. In some embodiments, the output of the trained inference model may be musculoskeletal position information that describes, for example, the positions and/or forces of elements in a computer-implemented musculoskeletal model. As neuromuscular signals are continuously recorded, the musculoskeletal model may be updated with predictions of the musculoskeletal position information output from the inference model. Control signals may then be generated based on the updated musculoskeletal position information. In other embodiments, the output of the trained inference model may be the control information itself, such that a separate musculoskeletal model is not used.

As discussed above, each muscle in the human body typically includes muscle fibers from hundreds of motor units. During normal motor control, in systems that generate control signals based on activation of one or more muscles (e.g., when a user activates a muscle or performs a movement using a group of muscles), the joint activity of the motor units within each muscle are projected to a single dimension corresponding to the activation or tension of that muscle. By projecting the multidimensional sensor signals to a single dimension, information about activation of individual sub-muscular structures (e.g., one or more motor units) is lost, as only the collective activation of all motor units within each muscle used to perform the movement, gesture or pose is considered when determining a corresponding control signal to generate. Some embodiments of the technology described herein are directed to using neuromuscular sensors to identify activation of sub-muscular structures and to generate a control signal based, at least in part, on the identified activated sub-muscular structure. The inventors have recognized and appreciated that by identifying activation of sub-muscular structures, a control system can be designed that includes multiple sub-muscular control "channels," each of which corresponds to pattern of activation identified within one or more motor units. Accordingly, information about sub-muscular structure activation, which is typically lost in conventional neuromuscular sensor-based control systems that project down to a single dimension, is utilized in some embodiments to increase the amount of control information that can be used to control a device. Additionally, by training a user to activate individual motor units or groups of motor units, some embodiments are configured to generate control information based on recorded neuromuscular signals without perceptible movement of muscles or groups of muscles.

Throughout this disclosure EMG sensors are used as examples of the type of neuromuscular sensors configured to detect neuromuscular activity. However it should be appreciated that other types of neuromuscular sensors including, but not limited to, mechanomyography (MMG) sensors, electrical impedance tomography (EIT) sensors, and sonomyography (SMG) sensors may additionally or alternatively be used in combination with EMG sensors to detect neuromuscular activity in accordance with some embodiments.

The neuromuscular signals recorded by the neuromuscular sensors may be used to identify activation of sub-muscular structures in accordance with the techniques described herein.

Figure 2:
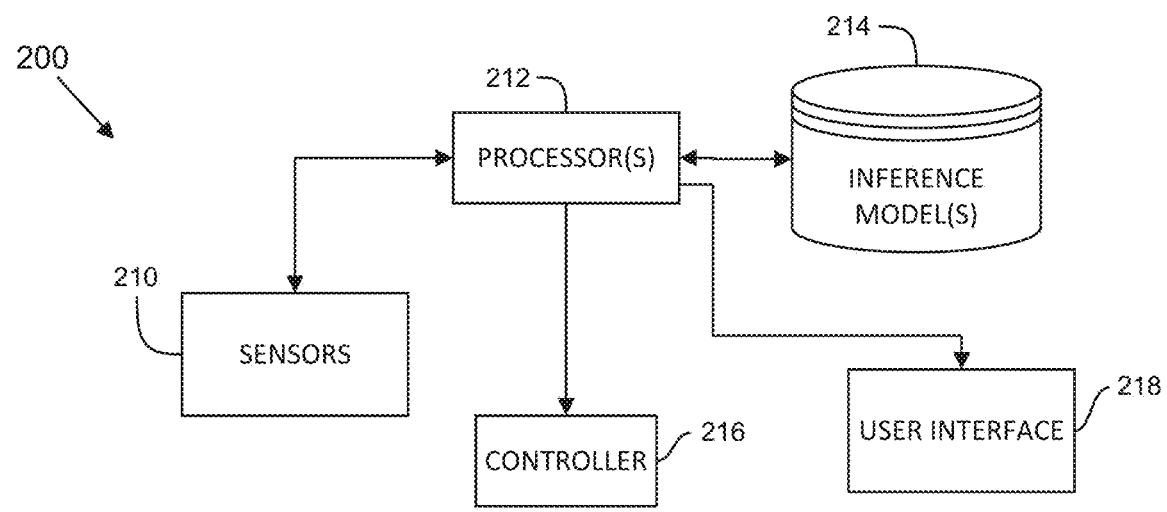
FIG. 2 is a schematic diagram of a computer-based system for generating sub-muscular control information in accordance with some embodiments of the technology described herein.

FIG. 2 illustrates a system 200 in accordance with some embodiments. The system includes a plurality of sensors 210 configured to record signals resulting from the activation of motor units with portions of a human body. Sensors 210 may include a plurality of neuromuscular sensors configured to record signals arising from neuromuscular activity in skeletal muscle of a human body, as described above. The term "neuromuscular activity" as used herein refers to neural activation of spinal motor neurons that innervate a muscle, muscle activation, muscle contraction, or any combination of the neural activation, muscle activation, and muscle contraction. In some embodiments, the plurality of neuromuscular sensors may be used to sense sub-muscular activity associated with a sub-muscular structure. In some embodiments, spatial information (e.g., position and/or orientation information) and force information describing the sub-muscular activation may be predicted based on the sensed neuromuscular signals as the user activates sub-muscular structures over time.

Sensors 210 may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect motor unit activity within one or more body segments distal to the torso (e.g., a forearm or wrist). It should be appreciated, however, that the sensors may be arranged in any suitable way, and embodiments of the technology described herein are not limited based on the particular sensor arrangement. For example, in some embodiments, at least one IMU and a plurality of neuromuscular sensors may be co-located on a body segment to track motor unit activity and/or movements of the body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine sub-muscular information associated with activation of sub-muscular structures in muscles of the wrist or hand.

Each of the sensors 210 includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, at least some of the plurality of sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the sensors may be arranged on a wearable patch configured to be affixed to a portion of the user's body. In some embodiments, multiple wearable devices, each having one or more IMUs and/or neuromuscular sensors included thereon may be used to generate control information based on activation from sub-muscular structures and/or movement that involve multiple parts of the body.

Figure 7:
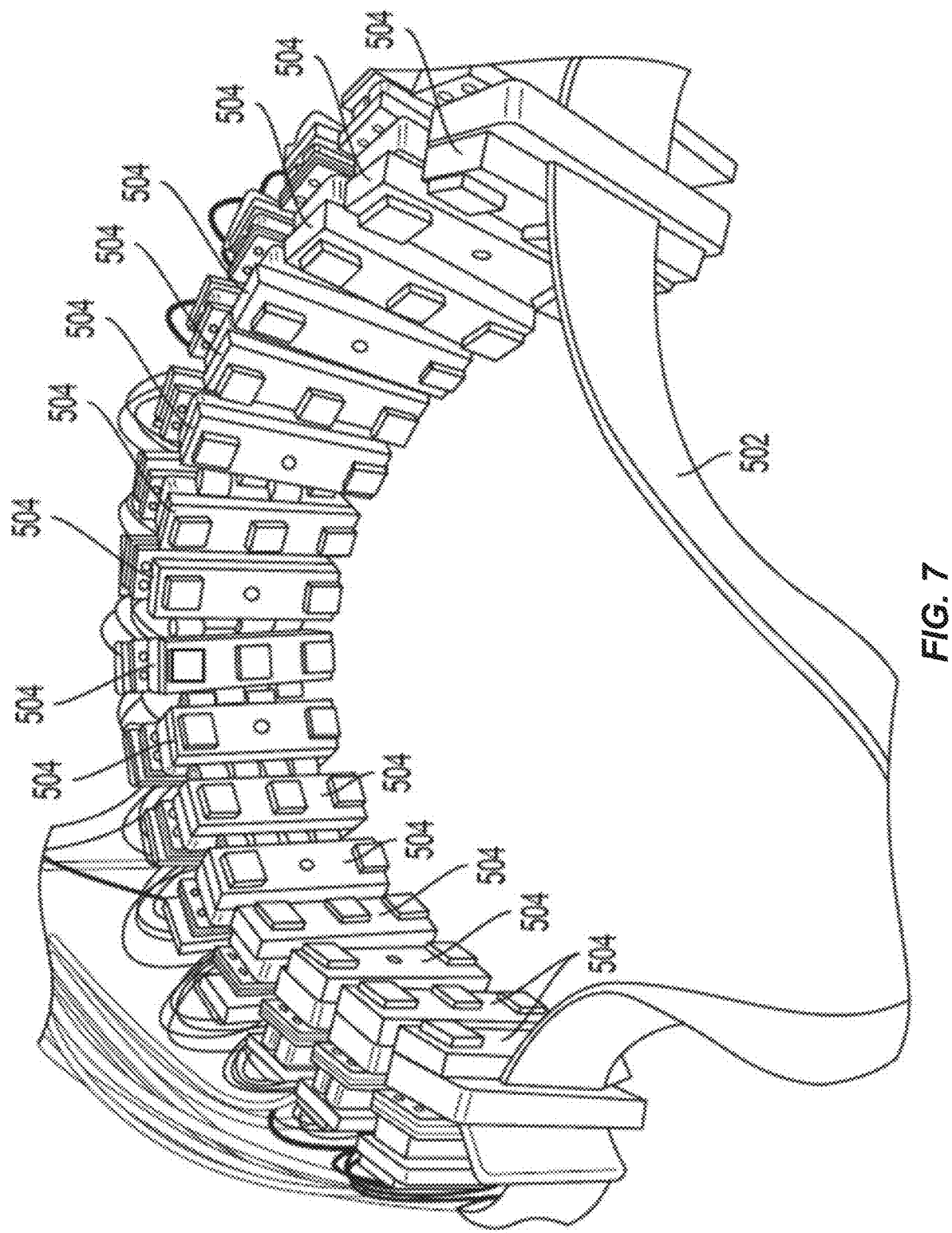
FIG. 7 illustrates a wristband/armband having EMG sensors arranged circumferentially thereon, in accordance with some embodiments of the technology described herein.
Figure 8:
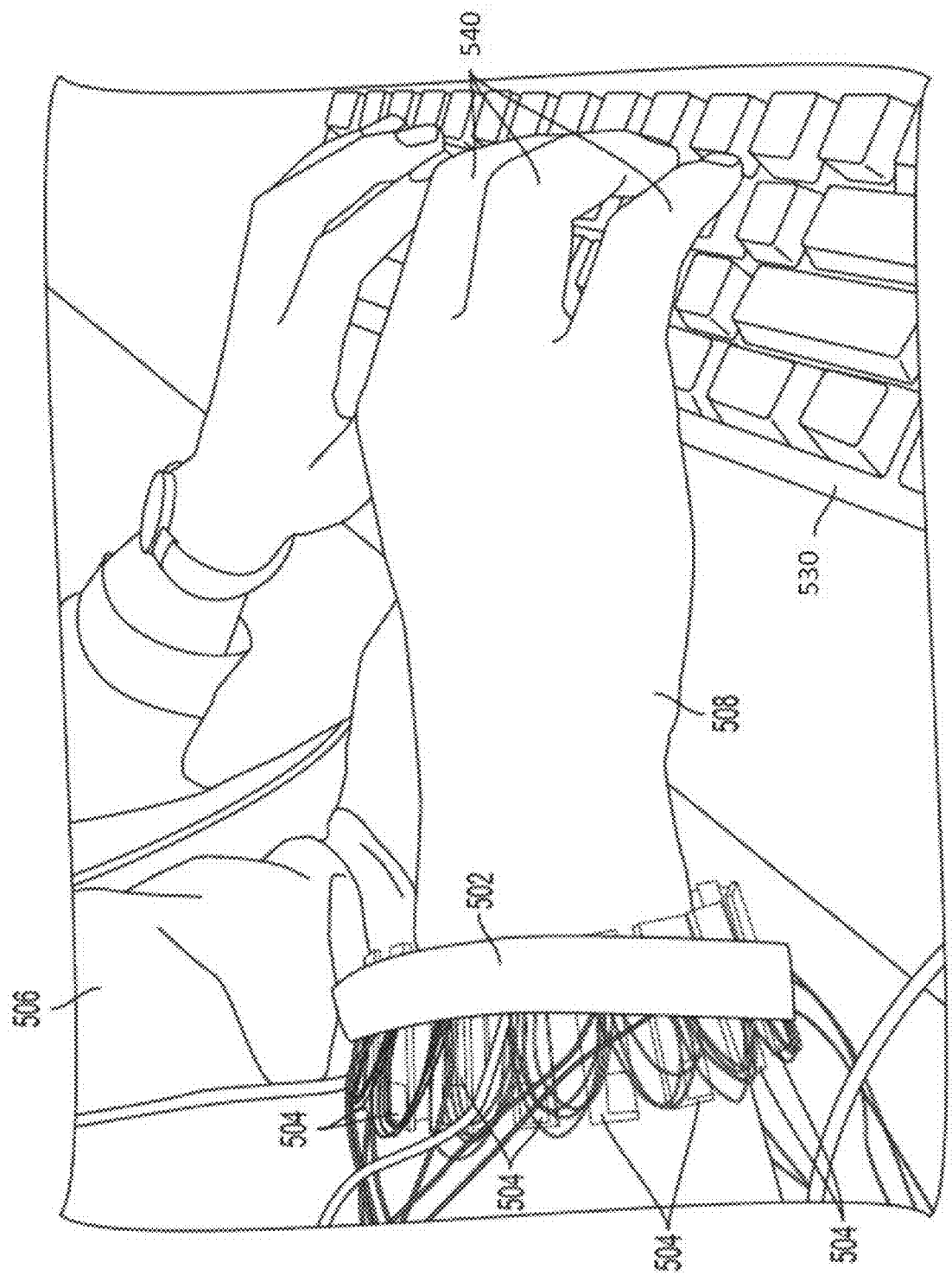
FIG. 8 illustrates a user wearing the wristband/armband of FIG. 7 while typing on a keyboard, in accordance with some embodiments of the technology described herein.

In one implementation, sixteen EMG sensors are arranged circumferentially around an elastic band configured to be worn around a user's lower arm. For example, FIG. 7 shows EMG sensors 504 arranged circumferentially around elastic band 502. It should be appreciated that any suitable number of neuromuscular sensors may be used and the number and arrangement of neuromuscular sensors used may depend on the particular application for which the wearable device is used. For example, a wearable armband or wristband may be used to generate control information for controlling a robot, controlling a vehicle, scrolling through text, controlling a virtual avatar, or any other suitable control task. For example, as shown in FIG. 8, a user 506 may be wearing elastic band 502 on hand 508. In this way, EMG sensors 504 may be configured to record EMG signals as a user controls keyboard 530 using fingers 540. In some embodiments, elastic band 502 may also include one or more IMUs (not shown), configured to record movement information, as discussed above.

In some embodiments, multiple wearable devices, each having one or more IMUs and/or neuromuscular sensors included thereon may be used to generate control information based on activation associated with sub-muscular structures and/or movement that involve multiple parts of the body.

In some embodiments, sensors 210 only include a plurality of neuromuscular sensors (e.g., EMG sensors). In other embodiments, sensors 210 include a plurality of neuromuscular sensors and at least one "auxiliary" sensor configured to continuously record a plurality of auxiliary signals. Examples of auxiliary sensors include, but are not limited to, IMU sensors, an imaging device (e.g., a camera), a radiation-based sensor for use with a radiation-generation device (e.g., a laser-scanning device), or other types of sensors such as a heart-rate monitor.

In some embodiments, the output of one or more of the sensing components may be optionally processed using hardware signal processing circuitry (e.g., to perform amplification, filtering, and/or rectification). In other embodiments, at least some signal processing of the output of the sensing components may be performed in software. Accordingly, signal processing of signals recorded by the sensors may be performed in hardware, software, or by any suitable combination of hardware and software, as aspects of the technology described herein are not limited in this respect.

In some embodiments, the recorded sensor data may be optionally processed to compute additional derived measurements that are then provided as input to an inference model, as described in more detail below. For example, recorded signals from an IMU sensor may be processed to derive an orientation signal that specifies the orientation of a body segment over time. Sensors may implement signal processing using components integrated with the sensing components, or at least a portion of the signal processing may be performed by one or more components in communication with, but not directly integrated with the sensing components of the sensors 210.

System 200 also includes one or more computer processors 212 programmed to communicate with sensors 210. For example, signals recorded by one or more of the sensors may be provided to the processor(s) 212, which may be programmed to execute one or more machine learning techniques to process signals output by the sensors 210 to train one or more inference models 214, and the trained (or retrained) inference model(s) 214 may be stored for later use in generating control signals, as described in more detail below.

In some embodiments, inference model 214 may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a gated recurrent neural network, a recursive neural network, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some embodiments, the output of the inference model provides discrete outputs. Discrete outputs (e.g., classification labels) may be used, for example, when a desired output is to know whether a particular pattern of activation (including individual neural spiking events) is currently being performed by a user. For example, the model may be trained to estimate whether the user is activating a particular motor unit, activating a particular motor unit with a particular timing, activating a particular motor unit with a particular firing pattern, or activating a particular combination of motor units. On a shorter timescale, discrete classification is used in some embodiments to estimate whether a particular motor unit fired an action potential within a given amount of time. In such a scenario, these estimates may then be accumulated to obtain an estimated firing rate for that motor unit.

In embodiments in which the inference model is implemented as a neural network configured to output a discrete signal, the neural network may include a softmax layer such that the outputs add up to one and may be interpreted as probabilities. The output of the softmax layer may be a set of values corresponding to a respective set of control signals, with each value indicating a probability that the user want to perform a particular control action. As one non-limiting example, the output of the softmax layer may be a set of three probabilities (e.g., 0.92, 0.05, and 0.03) indicating the respective probabilities that the detected pattern of activity is one of three known patterns.

It should be appreciated that when the inference model is a neural network configured to output a discrete signal, the neural network is not required to produce outputs that add up to one. For example, instead of a softmax layer, the output layer of the neural network may be a sigmoid layer (which has no restriction that the probabilities add up to one). In such embodiments, the neural network may be trained with a sigmoid cross-entropy cost. Such an implementation may be advantageous in the case when multiple different control actions may occur within a threshold amount of time and it is not important to distinguish the order in which these actions occur (e.g., a user may activate two patterns of neural activity within the threshold amount of time). In some embodiments, any other suitable non-probabilistic multi-class classifier may be used, as aspects of the technology described herein are not limited in this respect.

In some embodiments, the output of the inference model may be a continuous signal rather than a discrete signal. For example, the model may output an estimate of the firing rate of each motor unit or the model may output a time-series electrical signal corresponding to each motor unit or sub-muscular structure.

It should be appreciated that aspects of the technology described herein are not limited to using neural networks, as other types of inference models may be employed in some embodiments. For example, in some embodiments, the inference model may comprise a hidden Markov model (HMM), a switching HMM with the switching allowing for toggling among different dynamic systems, dynamic Bayesian networks, and/or any other suitable graphical model having a temporal component. Any such inference model may be trained using recorded sensor signals.

As another example, in some embodiments, the inference model is a classifier taking as input, features derived from the recorded sensor signals. In such embodiments, the classifier may be trained using features extracted from the sensor data. The classifier may be a support vector machine, a Gaussian mixture model, a regression based classifier, a decision tree classifier, a Bayesian classifier, and/or any other suitable classifier, as aspects of the technology described herein are not limited in this respect. Input features to be provided to the classifier may be derived from the sensor data in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the classifier.

In some embodiments, values for parameters of the inference model may be estimated from training data. For example, when the inference model is a neural network, parameters of the neural network (e.g., weights) may be estimated from the training data. In some embodiments, parameters of the inference model may be estimated using gradient descent, stochastic gradient descent, and/or any other suitable iterative optimization technique. In embodiments where the inference model is a recurrent neural network (e.g., an LSTM), the inference model may be trained using stochastic gradient descent and backpropagation through time. The training may employ a cross-entropy loss function and/or any other suitable loss function, as aspects of the technology described herein are not limited in this respect.

System 200 also optionally includes one or more controllers 216. For example, controller 216 may be a display controller configured to display a visual representation (e.g., of a hand) on a display. As discussed in more detail below, one or more computer processors may implement one or more trained inference models that receive as input sensor signals and provide as output information that is used to generate control signals.

In some embodiments, a computer application configured to simulate a virtual reality environment may be instructed to display a visual character such as an avatar (e.g., via controller 216). Positioning, movement, and/or forces applied by portions of visual character within the virtual reality environment may be displayed based on the output of the trained inference model(s). The visual representation may be dynamically updated as continuous signals are recorded by the sensors 210 and processed by the trained inference model(s) 104 to provide a computer-generated representation of the character's movement that is updated in real-time.

As discussed above, some embodiments are directed to using an inference model, at least in part, to map sensor signals to control signals. The inference model may receive as input IMU signals, neuromuscular signals (e.g., EMG, MMG, and SMG signals), external device signals (e.g., camera or laser-scanning signals), or a combination of IMU signals, neuromuscular signals, and external device signals detected as a user performs one or more sub-muscular activations. The inference model may be used to predict the control information without the user having to make perceptible movements.

In some embodiments, system 200 is trained to generate control information as the user performs sub-muscular activations. In some embodiments, system 200 is trained by recording signals from neuromuscular sensors 210 and ground truth data representing the corresponding control signal for a particular sub-muscular activation. For example, the user may be instructed to activate a sub-muscular structure to perform a particular control action.

Control signals may be generated based on a precise timing of sensed neural activation (temporal coding of detected spikes) or control signals may be generated based on rates of motor unit action potentials (rate coding).

The inventors have recognized that one of the challenges with using sub-muscular activations as the basis for generating control signals in a control system is training users how to selectively activate a single motor unit or a group of motor units. For example, an instruction to contract single muscles or groups of muscles to perform movement such as making a fist, may be easy for users to comprehend. However, instructing a user to selectively activate individual sub-muscular structures may not be as straightforward, and the user may need to be trained to perform such activations reliably. Accordingly, some embodiments are directed to techniques for providing feedback to a user during recording of neuromuscular signals to facilitate the process of training a user to activate sub-muscular structures (e.g., one or more motor units) when desired.

System 200 also optionally includes a user interface 218. Feedback determined based on the signals recorded by sensors 210 and processed by processor(s) 212 may be provided via user interface 218 to facilitate a user's understanding of how the system is interpreting the user's intended sub-muscular activation. User interface 218 may be implemented in any suitable way including, but not limited to, an audio interface, a video interface, a tactile interface, and electrical stimulation interface, or any combination of the foregoing.

Figure 3:
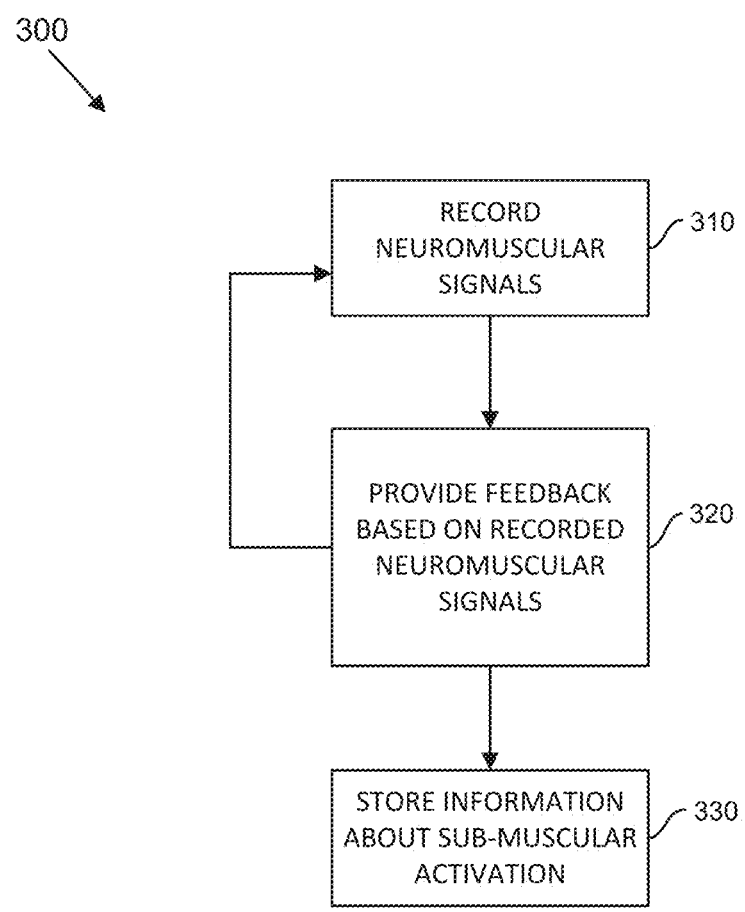
FIG. 3 is a flowchart of a process for training a user to activate sub-muscular structures in accordance with some embodiments of the technology described herein.

FIG. 3 illustrates a process 300 for training a user to activate sub-muscular structures using neuromuscular signals and feedback generated by processing the recorded signals in accordance with some embodiments. In act 310, a plurality of neuromuscular signals are recorded by a plurality of neuromuscular sensors worn by a user as the user activates one or more sub-muscular structures. Process 300 then proceeds to act 320 where feedback generated based on the recorded neuromuscular signals is provided to the user based on the recorded neuromuscular signals. The feedback may be provided via a user interface (e.g., user interface 218 in system 200). The feedback generated in act 320 provides information to the user about the recorded neuromuscular signals which in turn enables the user to learn how to selectively activate sub-muscular structures. Although feedback is described in connection with process 300 for training a user to activate sub-muscular structures, in some embodiments, feedback is provided to the user even after the system has been trained. Providing feedback as the user is using the system following training may facilitate the user's understanding of how the trained system is interpreting the user's intended sub-muscular activation and may alert the user as to whether further training of the system is needed.

In some embodiments, the feedback provided to the user in act 320 is generated using the raw (e.g., unprocessed) neuromuscular signals recorded by the neuromuscular sensors. For example, the raw neuromuscular signals may be converted into audio signals that are played through an audio interface (e.g., a speaker). Alternatively, the raw neuromuscular signals may be displayed on a visual interface such as a display to provide feedback. In other embodiments, the raw neuromuscular signals may be analyzed to identify activation of particular sub-muscular structures. The inventors have recognized and appreciated that activation of sub-muscular structures is manifested in neuromuscular signals in characteristic ways (e.g., timing, waveform shape) that enables the separation of signals arising from one sub-muscular structure from another sub-muscular structure. Identifying activation of particular sub-muscular structures from the raw neuromuscular signals may be performed in any suitable way. For example, the raw neuromuscular signals may be decomposed into signal components (e.g., using independent component analysis, convolutive blind source separation, spike sorting protocols that include event detection followed by clustering or classification, or another suitable technique) corresponding to activation arising from individual motor units (e.g., individual spiking events in a motor unit) or groups of motor units.

Characteristics or "signatures" of sub-muscular activation identified in the recorded neuromuscular signals may be used to generate feedback provided to the user as the user activates sub-muscular structures. For example, the user may be provided with audio feedback that encodes activation of different sub-muscular structures using audio having different characteristics. In a simplified example, the system may analyze raw neuromuscular signals and identify activation of two motor units. Audio feedback may be generated including a first audio tone having a first pitch and a second audio tone having a second pitch, where the first audio tone corresponds to activation of one of the two motor units and the second audio tone corresponds to activation of the other of the two motor units. In some embodiments, the timing of the presentation of tones in the audio feedback may correspond to a timing of activation (e.g., neuromuscular spike activity) for the corresponding motor unit or other sub-muscular structure. In some embodiments, the amplitude of the tone may correspond to the rate or intensity with which the sub-muscular structure is activated.

The feedback received by the user provides the user with information about whether and when the system is able to detect a pattern of neuromuscular activity associated with particular sub-muscular structures, and allows the user to adapt their neuromuscular activity to learn how to activate sub-muscular structures, such as a single motor unit. For example, if the user receives audio feedback that includes tones having multiple pitches, the user is made aware of the pattern of activity for multiple sub-muscular structures that the system has identified as being activated. Based on this feedback, the user can consciously modify their neuromuscular activity in an attempt to invoke a particular activation pattern associated with a sub-muscular structure. As the user modifies their motor activity, the feedback provided to the user also changes based on the recorded neuromuscular signals to enable the user to understand in real-time how modifications in their activity were interpreted by the system. The user can continue to continuously modify their activity based on the provided feedback to learn how to activate particular patterns of sub-muscular activity.

When audio signals are used as feedback, audio characteristics other than pitch of a tone may be used to signify differences between identified activated sub-muscular structures in the recorded neuromuscular signals. For example, loudness, duration, timbre, or other perceptual audio characteristics of the audio feedback may be modulated to represent the identification of particular sub-muscular structures in the neuromuscular signals. Additionally, audio signals other than tones may also be used. For example, different activated sub-muscular structures may be represented in the audio feedback by different musical instruments.

Feedback other than audio feedback may alternatively be used in accordance with some embodiments. Non-limiting examples of feedback that may be provided to a user to facilitate training a user to activate sub-muscular structures include visual feedback, tactile/haptic feedback, and feedback provided via electrical stimulation. For any chosen feedback modality, perceptual characteristics of components of the feedback provided may be updated in real-time based on sub-muscular activation identified in recorded neuromuscular signals to enable the user to learn how to modify their neuromuscular activity to activate one or more sub-muscular structures using particular activation patterns. For example, the user may be trained to alternate firings of two motor units, create a rhythmic pattern of firings for a single motor unit, or modulate the rate of one or more motor units in a time-dependent manner, and the feedback may be provided to facilitate the training.

As described above, feedback provided to a user may be generated based on raw (e.g., unprocessed) sensor data. In other embodiments, feedback may be generated based on information derived from the recorded sensor data. For example, the recorded sensor data may be filtered or otherwise processed prior to being used to generate feedback provided to the user.

As described above, some embodiments employ an inference model trained to output information used to generate a control signal based on sensor data provided as input to the model. In some embodiments, feedback provided to a user is generated based on an output of the trained inference model. For example, a control signal generated based on the output of the trained inference model may be provided to a display controller (or other suitable controller) that updates a display with information that informs the user about particular sub-muscular structures that were activated. As the user modifies their neuromuscular activation based on the feedback provided on the display, the control signal generated by the system is also updated, resulting in an updated visual representation on the display. In this way, the feedback provided to the user may be presented in a form that mimics a game that encourages the user to complete a particular task, where completion of the task is associated with successful activation of a particular pattern of sub-muscular activity. Such feedback may be more easily comprehensible and useful for some users, enabling those users to learn how to sub-muscular structures in particular ways.

Realizing that different users may learn how to activate sub-muscular structures in different ways, some embodiments provide feedback to users in multiple different ways. The user may be able to select the type of feedback that is most useful to facilitate their training. In some embodiments, the type of feedback that is provided to the user may be determined and/or recommended, at least in part, by the system, based on a measure of the effectiveness of the feedback to help the user learn. For example, a measure of how long it takes a user to successfully complete a task associated with activating a sub-muscular structure may be used to determine which type of feedback is recommended by the system for a particular user.

As shown in process 300, feedback may be provided continuously as the user learns to invoke a particular activation pattern and neuromuscular signals are continuously recorded as the user modifies their behavior in response to the feedback. The training may continue until it is determined that the user has successfully learned how to activate particular sub-muscular structures as desired (e.g., in a particular pattern). This determination may be made by the user or may be made, at least in part, using an automated process implemented, for example, using processor 212. For example, the signals recorded by the sensor may be compared to a template describing a known or desired activation pattern and when there is a sufficient match to the template, it may be determined to end the training for the particular sub-muscular activation pattern. The determination that a user has successfully trained a sub-muscular pattern may be made even when other sub-muscular structures or activity patterns are also observed in the recorded sensor data. For example, if the system is programmed to determine whether the user has activated motor unit A, it may be determined that the user has activated motor unit A when the system determines that motor units A, B and C (or other unidentified sources) have been activated, but not when the system determines that motor units C and D (but not A) have been activated. In some embodiments, the system is programmed to determine that the user has activated motor unit A when only motor unit A has been activated.

After it has been determined to stop training, process 300 proceeds to act 330 where information about the sub-muscular activation on which the user was training to activate is stored. In some embodiments, an inference model trained to map the recorded sensor data to one or more control signals associated with the sub-muscular structure may be stored and/or updated. For example, when the inference model is implemented as a neural network, the weights associated with the connections in the neural network may be updated to reflect the mapping between the recorded sensor data and a control signal output from or derived from output of the inference model.

The inventors have recognized that storing information about sub-muscular activation by a user enables the user to activate the same sub-muscular structure or structures across sessions. A second session of wearing a system with a plurality of neuromuscular sensors 210 and other components shown in FIG. 2 may occur minutes, hours, days, weeks, months, or even years after a first session. The stored representation of the sub-muscular activation by the user can be accessed and used as a control signal.

Figure 9A:
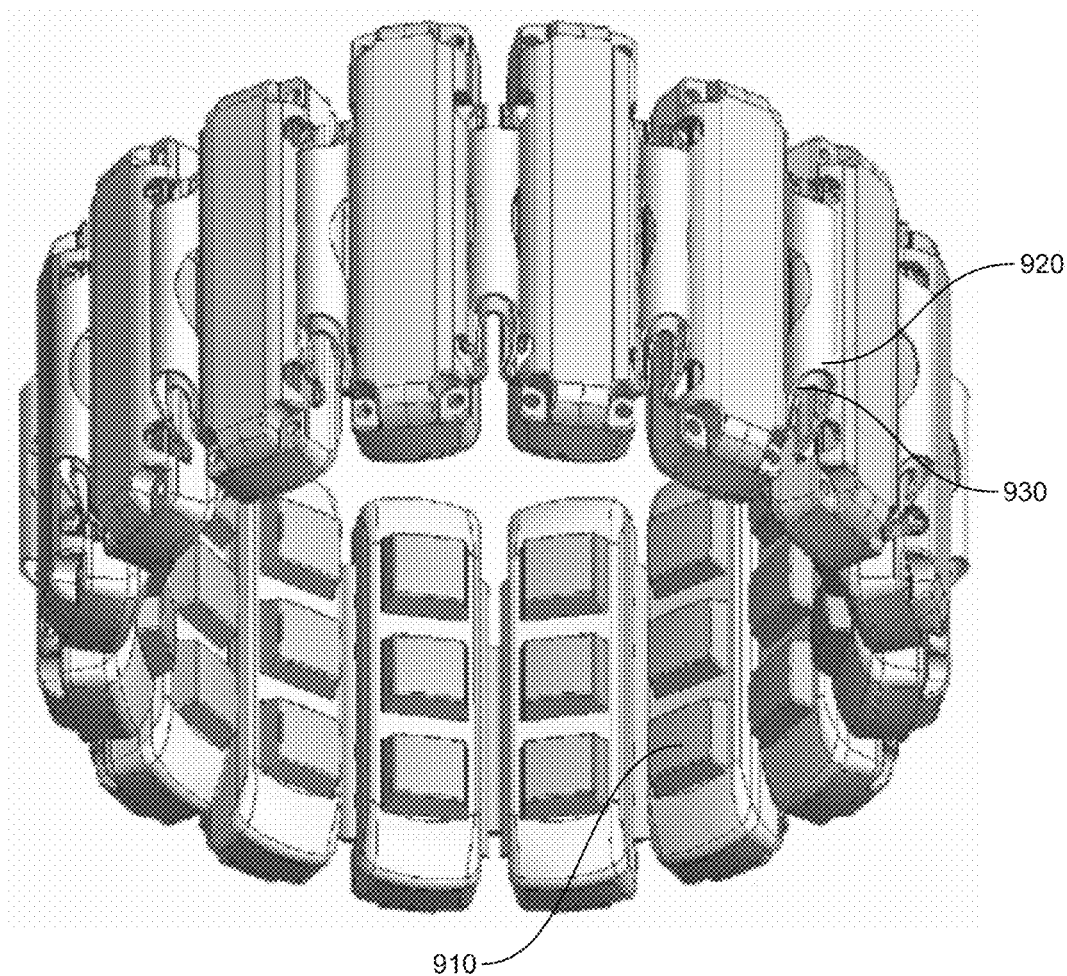
FIG. 9A illustrates a wearable system with sixteen EMG sensors arranged circumferentially around an elastic band configured to be worn around a user's lower arm or wrist, in accordance with some embodiments of the technology described herein.

In general, inference models may be implemented that calibrate the neuromuscular sensor data recorded from the user in order to reliably derive information for one or more sub-muscular structures activated by the user. Calibration may be necessary for several reasons. For example, calibration may be necessary because, when a user wears a neuromuscular array in a second session, one or more of the neuromuscular sensors may be in a different position on the user's body than in the first session. When the neuromuscular sensors are arranged in a radial array on the wearable device as shown in FIGS. 7 and 9A, the location of the neuromuscular sensors on the body may rotate from session to session, and an inference model may be used to calibrate the neuromuscular sensor data in order to reliably identify the same sub-muscular structure (or structures) identified in the first session. In another example of why calibration may be necessary, the position of a radial neuromuscular array (e.g., the system shown in FIGS. 7 and 9A) may be located more distal or proximal on an arm of the user, and an inference model may be used to calibrate the neuromuscular sensor data in order to reliably identify the same sub-muscular structure (or structures) identified in the first session. In yet another example of why calibration may be necessary, a radial neuromuscular array (e.g., the system shown in FIGS. 7 and 9A) may be placed on the user's arm in the opposite orientation—that is, a side of the neuromuscular array that faced proximally in a first session may face distally in a second session, and an inference model may be used to identify whether the neuromuscular array is facing proximally or distally and the anatomical position of the neuromuscular sensors may be re-ordered in a processing step that precedes identification of the previously identified sub-muscular structure or structures.

The inventors have recognized that systems and methods that store information about sub-muscular activation by a user that enable the user to activate the same sub-muscular structure or structures across sessions are beneficial for identifying changes in sub-muscular activation across time in a user. Tracking changes in sub-muscular activation is beneficial for monitoring changes in the motor nervous system of the user. Changes in sub-muscular activation may change for any of several reasons, including but not limited to: muscle fatigue, training to strengthen or otherwise affect the pattern of sub-muscular activation (e.g., motor learning or strength training), diet, time-of-day, the amount and quality of sleep a user has had, the presence of compounds that affect the motor nervous system (e.g., pharmaceutical agents, drugs of abuse, caffeine, alcohol, and nicotine), peripheral neuropathy, neurodegeneration, peripheral nerve injury, brain injury, or other disorder that affects the motor system.

The inventors have recognized that while some users may be able to selectively activate sub-muscular structures while suppressing other neural activity, other users may have difficulty learning to selectively activate sub-muscular structures. In some embodiments, a control signal output from the system is mapped to a subset of motor units activated during a motor task (e.g., moving a hand up and down), wherein the subset of motor units are associated with a sub-muscular structure. During training, the user may initially move their hand up and down, thereby activating the motor units in the subset mapped to the control signal in addition to other motor units. Over time, the user may learn that producing smaller and smaller movements still results in the control signal being output from the system as long as the user's movements still activate the motor units in the subset. Eventually, with additional training the user may be able to generate the control signal without making perceptible movements as long as the motor units in the subset corresponding to the sub-muscular structure are activated. Training a user to make small movements to activate sub-muscular structures in accordance with some embodiments enables the creation of a control system in which user fatigue is reduced and in which the user can control a device discretely (e.g., when the user is in a place where making larger movements to generate control signals is not appropriate behavior) or independently of larger movements.

As discussed briefly above, activation of a particular sub-muscular structure may be observed in recorded sensor data as timings and/or signal waveform shapes that characterize the activation from that structure. The spatiotemporal activation patterns that characterize activation of a sub-muscular structure are also referred to herein as the structure's "signature." The ability of the system to effectively separate activations from different sub-muscular structures, and thus create separate control channels for activation associated with individual sub-muscular structures or multiple sub-muscular structures (e.g., combinatorial codes), may depend on how different the signatures are for the sub-muscular structures. Additionally, the set of sub-muscular structures whose signatures achieve the best separation may vary from user to user. Prior to training a user how to activate sub-muscular patterns of activation, a set of target sub-muscular structures that the user may be trained to activate may be identified.

Figure 4:
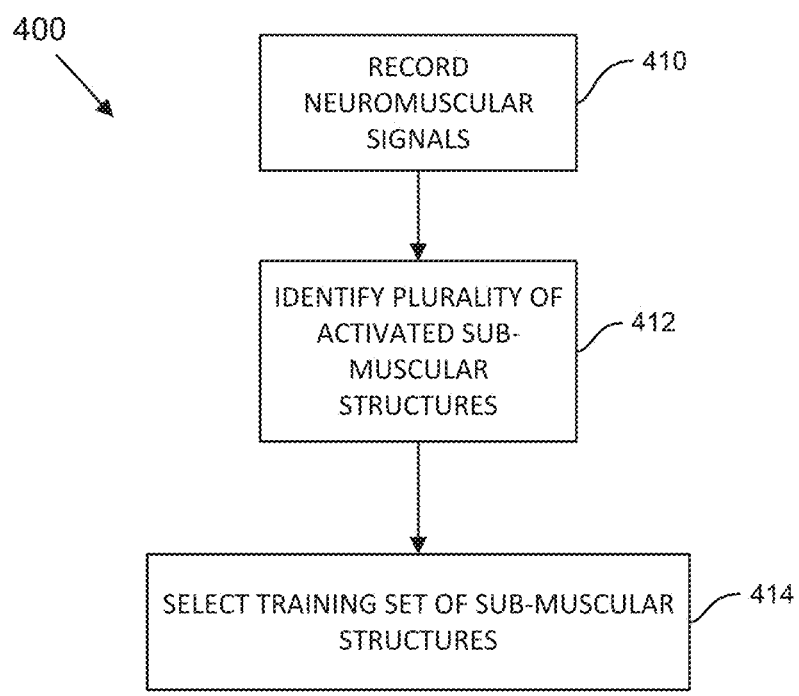
FIG. 4 is a flowchart of a process for selecting a set of sub-muscular structures for training in accordance with some embodiments of the technology described herein.

FIG. 4 illustrates a process 400 for identifying a set of sub-muscular structures to be used as training targets in accordance with some embodiments. In act 410, a plurality of neuromuscular signals is recorded from a plurality of sensors arranged on a wearable device as the user performs one or more movements or gestures. Process 400 then proceeds to act 412 where a plurality of activated sub-muscular structures (e.g., motor units) are identified based on the recorded neuromuscular signals. The plurality of activated sub-muscular structures may be identified in any suitable way. For example, the recorded neuromuscular signals may be decomposed into signal components that characterize activation of the plurality of activated sub-muscular structures. In some embodiments, the signal components may represent individual spiking events and identifying the plurality of activated sub-muscular structures may be performed by determining which of the individual spiking events are associated with activation of particular sub-muscular structures. Alternatively, the recorded neuromuscular signals may be analyzed in any other suitable way to identify a plurality of sub-muscular structures.

Process 400 then proceeds to act 414, where a subset of sub-muscular structures is selected for use in training. Selection of sub-muscular structures to include in the training set may be based, at least in part, on characteristics of activation associated with each of the sub-muscular structures identified in act 412. As described above, to enable the system to distinguish between activation of different sub-muscular structures, the inventors have recognized that it is advantageous to train users to activate sub-muscular structures having different activation characteristics or signatures as manifested in the recorded sensor data. Examples of characteristics of activation that may be used in some embodiments to select sub-muscular structures to include in a training set include, but are not limited to, a type of motor unit associated with the sub-muscular structure, a motor unit action potential amplitude associated with the sub-muscular structure, a similarity of a waveform for activation of the sub-muscular structure to waveforms for activation of other sub-muscular structures, and activation rate and timing statistics associated with activation of the sub-muscular structure.

In some embodiments, the number of sub-muscular structures to include in the training set are determined based on a desired number of sub-muscular control channels for the control system. For example, to construct a neuromuscular-based control system with eight sub-muscular control channels, the plurality of activated sub-muscular structures identified in act 412 may be analyzed to determine eight activated sub-muscular structures that have reliably separable characteristics of activation to include in the training set. It should be appreciated that not all of the sub-muscular structures selected for inclusion in the training set need be separable from other sub-muscular structures in the training set using the same activation characteristics. For example, a first sub-muscular structure in the training set may be separable from other structures in the training set based on signal waveform shape, whereas a second sub-muscular structure in the training set may be separable from other structures in the training set based motor unit action potential amplitude. Additionally, it should be appreciated that the sub-muscular structures selected for the training set may be separable based on a combination of characteristics of activation, and embodiments are not limited in this respect.

Selection of sub-muscular structures in act 414 may be automatically performed by the one or more processors of the system 100 using criteria that maximize or increase the distance between activation characteristics or signatures of the activated sub-muscular structures. Alternatively, the selection of sub-muscular structures may be at least partially user driven. For example, users may be provided with feedback generated based on the recorded neuromuscular signals and the users may be able to select the sub-muscular structures to include in the training set. Permitting users to participate in the process of selecting sub-muscular structures allows the control system to implement a less robust source separation technique than would be required if the selection of sub-muscular structures for the training set was entirely automated by the system.

Following selection of a set of sub-muscular structures for the training set, the user may be trained to activate each of the sub-muscular structures in the set using, for example, training process 300 shown in FIG. 3 and described above. Spatiotemporal information about the activated sub-muscular structures in the training set and/or the information that maps neuromuscular sensor signals to sub-muscular activation (e.g., a user-specified or trained inference model) may be stored by at least one storage device associated with the system for using the system to control a device once the user and the system have been trained.

The inventors have recognized that each time the user wears the wearable device including the neuromuscular sensors to begin a control session, it may be difficult, at least initially, for the system to recover activity from the same sub-muscular structures on which the system was trained. For example, the placement on the body of the wearable device including the sensors may be different each time the user uses the device. Accordingly, prior to using the system, including the trained inference model, to control a device, the system may be calibrated. The calibration may be automatically performed by the system when the user starts using the device or the calibration may be at least partially user-driven to relax the requirement that the system perform automatic calibration without user input. Additionally, it should be appreciated that calibration may be performed at any suitable time including during a control session.

Figure 5:
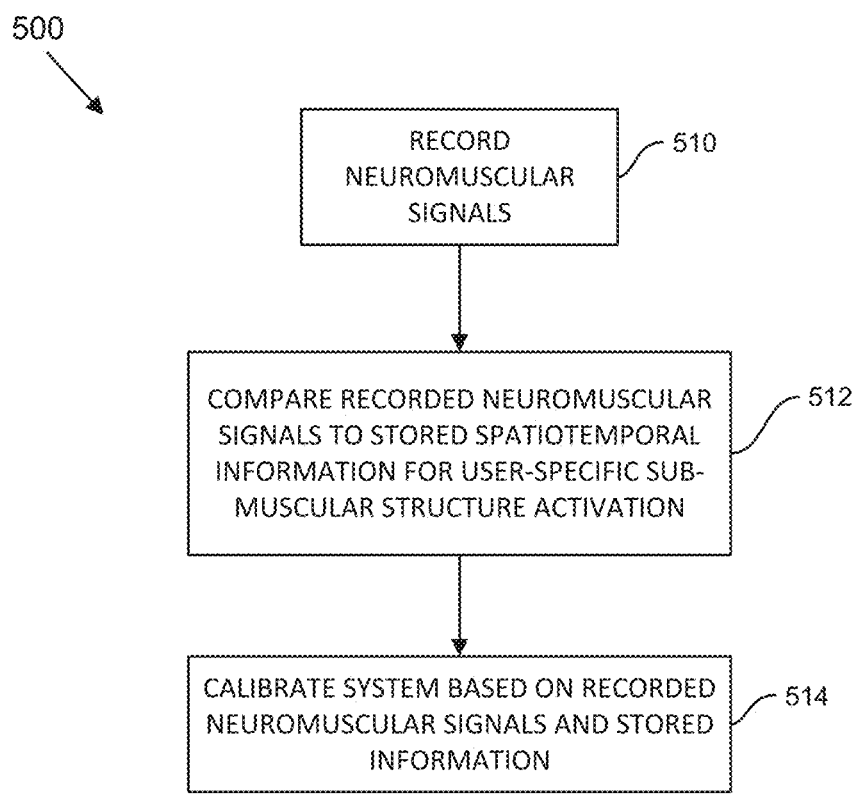
FIG. 5 is a flowchart of a process for calibrating a control system in accordance with some embodiments of the technology described herein.

FIG. 5 shows a process 500 for calibrating the system in accordance with some embodiments. In act 510, neuromuscular signals are recorded from sensors arranged on a wearable device worn by a user. Process 500 then proceeds to act 512, where the recorded neuromuscular signals are compared to information stored during the training process described above in connection with FIG. 3. For example, the system may analyze the recorded neuromuscular signals to determine whether the system can automatically identify activation of sub-muscular structures using spatiotemporal information about the sub-muscular structures in the training set. The system may be configured to automatically identify the sub-muscular structures in the recorded sensor data by, for example, performing source separation on the recorded neuromuscular signals.

In embodiments in which the one or more processors of the system are not configured to perform automatic calibration, or in the case where automatic calibration fails, the user may provide input to facilitate the calibration process. For example, the user may be prompted to activate a plurality of sub-muscular structures in sequence, e.g., structure A, structure B, structure C. Feedback may be provided to the user as the user activates each of the sub-muscular structures to let the user know whether the system correctly interpreted the intended activation.

Process 500 then proceeds to act 514, where the system is calibrated based on the analysis of the recorded neuromuscular signals and the stored information. Calibration may be performed in any suitable way to enable the system to recover activation of the sub-muscular structures in the training set from the recorded neuromuscular signals. In some embodiments, the calibration may include transforming some of the recorded neuromuscular signals or information derived from the recorded neuromuscular signals to a representation that more closely aligns with the stored information. In other embodiments, the user may be provided with feedback instructing the user to adjust the positioning of the wearable device on the body and additional neuromuscular signals may be recorded until the system is able to reliably recover activation of the sub-muscular structures from the recorded sensor data.

After the system has been calibrated, the system may be used to derive information for a plurality of sub-muscular control channels from recorded signal data, generate control signal(s) based on the derived information, and provide the control signal to a control interface to control operation of a physical or virtual device. In this way, a control system capable of controlling a device using sub-muscular activation is provided.

Figure 6:
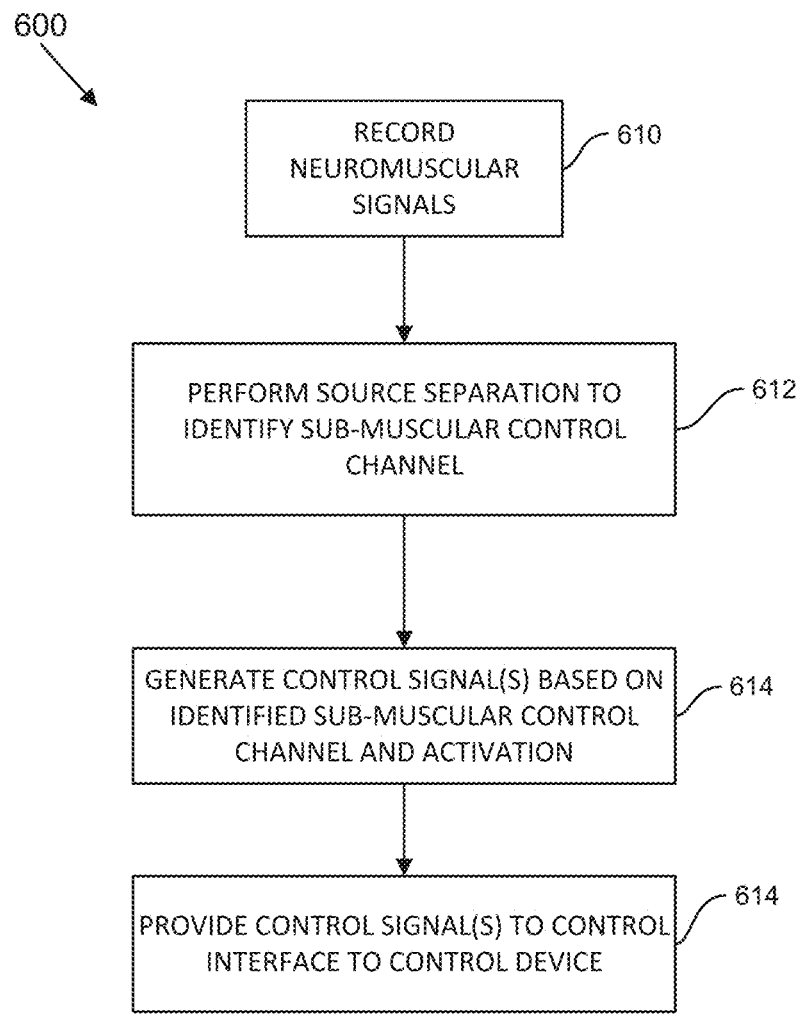
FIG. 6 is a flowchart of a process for using a calibrated control system to provide a control signal based on sub-muscular activation in accordance with some embodiments of the technology described herein.

FIG. 6 illustrates a process 600 for providing a control signal to a device based on sub-muscular control information recorded from sensor data in accordance with some embodiments. In act 610, a plurality of neuromuscular signals is recorded from neuromuscular sensors arranged near or on the surface of a user's body. One or more auxiliary sensors (e.g., IMU sensors) may also be used to record sensor data used for providing control information, and embodiments are not limited in this respect. Process 600 then proceeds to act 612 where a source separation process is performed on the recorded neuromuscular signals to identify a sub-muscular control channel associated with activation identified in the neuromuscular signals. Any suitable source separation technique, examples of which are discussed above, may be used to identify a sub-muscular control channel.

Process 600 then proceeds to act 614 where one or more control signals are generated based on the identified sub-muscular control channel and a pattern of activation represented in the recorded neuromuscular signals. For example, the neuromuscular signals may be provided as input to a trained inference model and an output of the trained inference model may be used to generate one or more control signals. In one implementation, the output of the trained inference model may be a set of one or more control signals. In another implementation, the control signal(s) may be generated based on the pattern of activation in the neuromuscular signals without the use of a trained inference model. Process 600 then proceeds to act 614 where the control signal(s) are provided to a control interface of a device to control an operation of the device. For example, the device may be a display and a control signal may be provided to a display controller of the display. The control signal may include instructions to update information displayed on the display. Alternatively, the device may be a computer or other computing device (e.g., a smartphone) and the control signal may be provided to a controller of the computing device to change an operation of the device. In yet a further example, the control signal may be used to control a device (e.g., a musical instrument) to provide an artistic expression. It should be appreciated that any device having a control interface may be controlled using control systems designed in accordance with the techniques described herein.

Figure 9B:
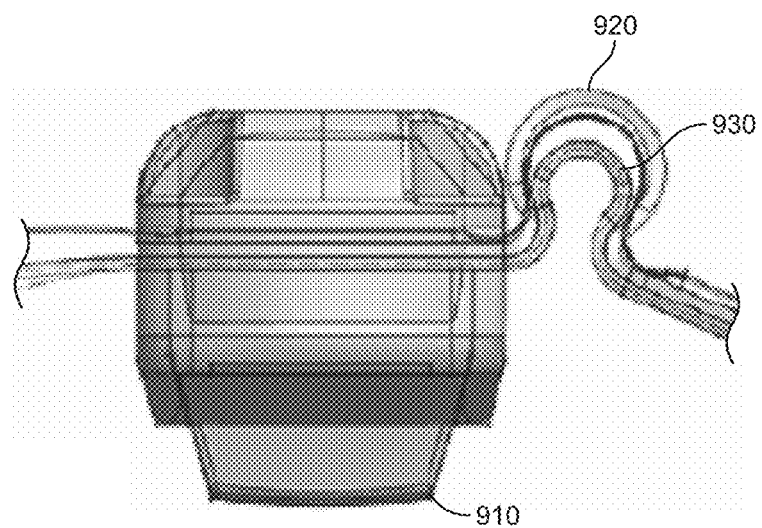
FIG. 9B is a cross-sectional view through one of the sixteen EMG sensors illustrated in FIG. 9A.

FIG. 9A illustrates a man-machine interface (also referred to herein as an EMG control interface) as a wearable system with sixteen neuromuscular sensors 910 (e.g., EMG sensors) arranged circumferentially around an elastic band 920 configured to be worn around a user's lower arm or wrist. As shown, EMG sensors 910 are arranged circumferentially around elastic band 920. It should be appreciated that any suitable number of neuromuscular sensors may be used. The number and arrangement of neuromuscular sensors may depend on the particular application for which the wearable system is used. For example, a wearable armband or wristband can be used to generate control information for controlling an augmented reality system, a robot, controlling a vehicle, scrolling through text, controlling a virtual avatar, or any other suitable control task. As shown, the sensors may be coupled together using flexible electronics incorporated into the wireless device, FIG. 9B illustrates a cross-sectional view through one of the sensors of the wearable system shown in FIG. 9A.

In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 910 are discussed in more detail below with reference to FIGS. 10A and 10B.

Figure 10A:
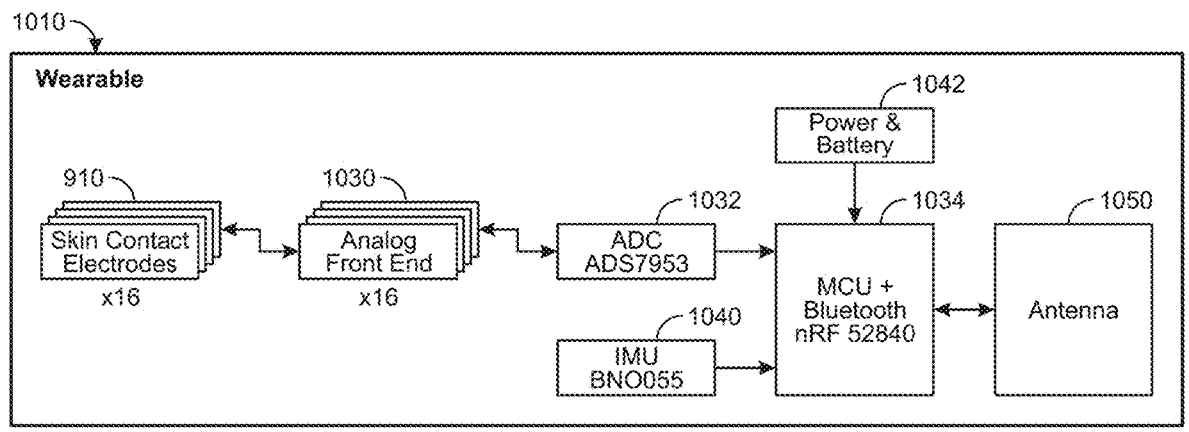
FIGS. 10A and 10B schematically illustrate components of a computer-based system on which some embodiments are implemented.
Figure 10B:
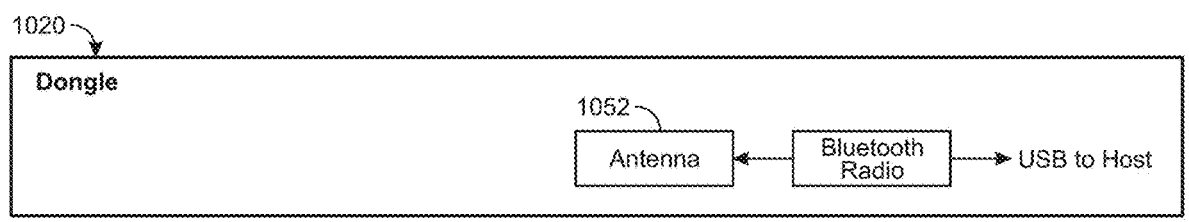

FIGS. 10A and 10B illustrate a schematic diagram with internal components of a wearable system with sixteen EMG sensors. As shown, the wearable system includes a wearable portion 1010 (FIG. 10A) and a dongle portion 1020 (FIG. 10B) in communication with the wearable portion 1010 (e.g., via Bluetooth or another suitable short range wireless communication technology). As shown in FIG. 10A, the wearable portion 1010 includes sensors 910, examples of which are described in connection with FIGS. 9A and 9B. The output of the sensors 910 is provided to analog front end 1030 configured to perform analog processing (e.g., noise reduction, filtering, etc.) on the recorded signals. The processed analog signals are then provided to analog-to-digital converter 1032, which converts the analog signals to digital signals that can be processed by one or more computer processors. An example of a computer processor that may be used in accordance with some embodiments is microcontroller (MCU) 1034 illustrated in FIG. 10A. As shown, MCU 1034 may also include inputs from other sensors (e.g., IMU sensor 1040), and power and battery module 1042. The output of the processing performed by MCU may be provided to antenna 1050 for transmission to dongle portion 1020 shown in FIG. 10B.

Dongle portion 1020 includes antenna 1052 configured to communicate with antenna 1050 included as part of wearable portion 1010. Communication between antenna 1050 and 1052 may occur using any suitable wireless technology and protocol, non-limiting examples of which include radiofrequency signaling and Bluetooth. As shown, the signals received by antenna 1052 of dongle portion 1020 may be provided to a host computer for further processing, display, and/or for effecting control of a particular physical or virtual object or objects.

Although the examples provided with reference to FIGS. 9A, 9B and FIGS. 10A, 10B are discussed in the context of interfaces with EMG sensors, it is understood that the techniques described herein for reducing electromagnetic interference can also be implemented in wearable interfaces with other types of sensors including, but not limited to mechanomyography (MMG) sensors, sonomyography (SMG) sensors, and electrical impedance tomography (EIT) sensors.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A computerized system, comprising:
a plurality of neuromuscular sensors configured to record a plurality of neuromuscular signals from a user, wherein the plurality of neuromuscular sensors are arranged on one or more wearable devices; and
at least one computer processor programmed to:
separate the plurality of neuromuscular signals into a plurality of signal components characterizing a plurality of sub-muscular control channels, wherein each sub-muscular control channel is associated with activation of one or more sub-muscular structures, and the one or more sub-muscular structures are selected from the group consisting of an individual motor unit and a group of motor units;
associate a first sub-muscular control channel of the plurality of sub-muscular control channels with a first set of one or more signal components from the plurality of signal components;
generate a control signal for the first sub-muscular control channel, wherein the control signal is based on information derived from a pattern of activation associated with the first set of one or more signal components; and
provide the generated control signal to a control interface to control an operation of a device.

2. The computerized system of claim 1, wherein the at least one computer processor is further programmed to:
provide, as input to a trained inference model, the derived information for the first sub-muscular control channel, and wherein generating the control signal comprises generating the control signal based on the output of the trained inference model.

3. The computerized system of claim 1, wherein the at least one computer processor is further programmed to:
provide as input to a trained inference model, the signal components characterizing the plurality of sub-muscular control channels, and wherein deriving information for the first sub-muscular control channel comprises deriving the information based on processing of the signal components characterizing the plurality of sub-muscular control channels by the trained inference model.

4. The computerized system of claim 1, wherein the first sub-muscular control channel is configured to process information arising from activation of an individual motor unit.

5. The computerized system of claim 4, wherein a second sub-muscular control channel of the plurality of sub-muscular control channels is configured to process information arising from activation of a group of motor units.

6. The computerized system of claim 1, wherein the first sub-muscular control channel is configured to process information arising from activation of a combination of at least one first sub-muscular structure associated with a first muscle and at least one second sub-muscular structure associated with a second muscle.

7. The computerized system of claim 1, further comprising at least one auxiliary sensor configured to record an auxiliary signal simultaneously with the recording of the plurality of neuromuscular signals from the user, wherein the at least one auxiliary sensor is arranged on the one or more wearable devices.

8. The computerized system of claim 7, wherein the at least one auxiliary sensor comprises at least one inertial measurement unit.

9. The computerized system of claim 1, wherein the at least one computer processor is further programmed to:
store a representation of the derived information for the first sub-muscular control channel determined during a first session; and
calibrate neuromuscular signal data recorded from the user during a second session after the first session, wherein the calibration is performed based, at least in part, on the stored representation of the derived information for the first sub-muscular control channel determined during the first session.

10. A computer-implemented method of controlling a device, the method comprising:
receiving a plurality of neuromuscular signals recorded from a plurality of neuromuscular sensors arranged on one or more wearable devices worn by a user;
separating the plurality of neuromuscular signals into a plurality of signal components characterizing a plurality of sub-muscular control channels, wherein each sub-muscular control channel is associated with activation of one or more sub-muscular structures, and the one or more sub-muscular structures are selected from the group consisting of an individual motor unit and a group of motor units;
associating a first sub-muscular control channel of the plurality of sub-muscular control channels with a first set of one or more signal components from the plurality of signal components signal components characterizing the plurality of sub-muscular control channels, information for a first sub-muscular control channel of the plurality of sub- muscular control channels;
generating a control signal for the first sub-muscular control channel, wherein the control signal is based on information derived from a pattern of activation associated with the first set of one or more signal components; and
providing the generated control signal to a control interface to control an operation of a device.

11. The computer-implemented method of claim 10, further comprising providing, as input to a trained inference model, the derived information for the first sub-muscular control channel, and wherein generating the control signal comprises generating the control signal based on the output of the trained inference model.

12. The computer-implemented method of claim 10, further comprising providing, as input to a trained inference model, the signal components characterizing the plurality of sub-muscular control channels, and wherein deriving information for the first sub-muscular control channel comprises deriving the information based on processing of the signal components characterizing the plurality of sub-muscular control channels by the trained inference model.

13. The computer-implemented method of claim 10, wherein the first sub-muscular control channel is configured to process information arising from activation of an individual motor unit.

14. The computer-implemented method of claim 13, wherein a second sub-muscular control channel of the plurality of sub-muscular control channels is configured to process information arising from activation of a group of motor units.

15. The computer-implemented method of claim 10, wherein the first sub-muscular control channel is configured to process information arising from activation of a combination of at least one first sub-muscular structure associated with a first muscle and at least one second sub-muscular structure associated with a second muscle.

16. The computer-implemented method of claim 10, wherein at least one auxiliary sensor is configured to record an auxiliary signal simultaneously with the recording of the plurality of neuromuscular signals from the user, and wherein the at least one auxiliary sensor is arranged on the one or more wearable devices.

17. The computer-implemented method of claim 16, wherein the at least one auxiliary sensor comprises at least one inertial measurement unit.

18. The computer-implemented method of claim 10, further comprising:
    storing a representation of the derived information for the first sub-muscular control channel determined during a first session; and
    calibrating neuromuscular signal data recorded from the user during a second session after the first session, wherein the calibration is performed based, at least in part, on the stored representation of the derived information for the first sub-muscular control channel determined during the first session.

19. A non-transitory computer-readable medium comprising one or more computer-executable instructions that, when executed by at least one processor of a computing device, cause the computing device to:
    receive a plurality of neuromuscular signals recorded from a plurality of neuromuscular sensors arranged on one or more wearable devices worn by a user;
    separate the plurality of neuromuscular signals into a plurality of signal components characterizing a plurality of sub-muscular control channels, wherein each sub-muscular control channel is associated with activation of one or more sub-muscular structures, and the one or more sub-muscular structures are selected from the group consisting of an individual motor unit and a group of motor units;
    associate a first sub-muscular control channel of the plurality of sub-muscular control channels with a first set of one or more signal components from the plurality of signal components;
    generate a control signal for the first sub-muscular control channel, wherein the control signal is based on information derived from a pattern of activation associated with the first set of one or more signal components; and
    provide the generated control signal to a control interface to control an operation of a device.

20. The computer-readable medium of claim 19, further comprising providing, as input to a trained inference model, the derived information for the first sub-muscular control channel, and wherein generating the control signal comprises generating the control signal based on the output of the trained inference model.

* * * * *